United States Patent [19]

Desai et al.

[11] Patent Number: 5,098,915

[45] Date of Patent: Mar. 24, 1992

[54] SUBSTITUTED N-BENZYLPIPERIDINE AMIDES

[75] Inventors: Bipinchandra N. Desai, Vernon Hills; Kerry W. Fowler, Chicago, both of Ill.; Alan E. Moormann, Fort Collins, Colo.

[73] Assignee: G. D. Searle & Co., Chicago, Ill.

[21] Appl. No.: 403,205

[22] Filed: Sep. 5, 1989

[51] Int. Cl.[5] .................. A61K 31/445; C07D 401/06; C07D 401/12

[52] U.S. Cl. .................... 514/324; 514/318; 514/320; 514/326; 514/329; 546/193; 546/194; 546/196; 546/202; 546/205; 546/207; 546/212; 546/213; 546/214; 546/224; 546/237

[58] Field of Search ............ 546/193, 194, 196, 202, 546/205, 207, 212, 213, 214, 237, 224; 514/318, 320, 324, 326, 329

[56] References Cited

U.S. PATENT DOCUMENTS

| | | |
|---|---|---|
| 3,907,810 | 9/1975 | Cavalla .................. 546/210 |
| 3,910,931 | 10/1975 | Cavalla .................. 546/206 |
| 3,910,932 | 10/1975 | Cavalla .................. 546/194 |
| 3,912,741 | 10/1975 | Cavalla .................. 546/202 |
| 3,917,614 | 11/1975 | Cavalla .................. 546/208 |
| 3,919,242 | 11/1975 | Cavalla .................. 546/197 |
| 4,028,365 | 6/1977 | Cavalla .................. 546/200 |
| 4,029,801 | 6/1977 | Cavalla .................. 514/329 |
| 4,045,444 | 8/1977 | Cavalla .................. 546/197 |
| 4,046,767 | 9/1977 | Cavalla .................. 546/197 |
| 4,061,640 | 12/1977 | Cavalla .................. 546/175 |
| 4,138,492 | 2/1979 | Noverola .................. 546/213 |
| 4,277,501 | 7/1981 | Melley .................. 514/654 |
| 4,289,781 | 9/1981 | Bengtsson .................. 546/200 |
| 4,596,827 | 6/1986 | Melley .................. 514/605 |

FOREIGN PATENT DOCUMENTS

1345872 2/1974 United Kingdom .

OTHER PUBLICATIONS

Fleming, J. S., "Effects . . . Antihypertensive Agent," *Federation Proceedings*, vol. 43, p. 553, 1984.

*Primary Examiner*—Mary C. Lee
*Assistant Examiner*—Jacqueline Haley
*Attorney, Agent, or Firm*—Joy Ann Serauskas; Paul D. Matukaitis

[57] ABSTRACT

Substituted N-benzylpiperidine amides, which have activity as Class III antiarrhythmic agents, acting by prolonging cardiac action potential repolarization. The invention further provides for compositions incorporating the compunds and methods of their use, as well as providing for pharmaceutically acceptable salts of the compounds.

139 Claims, No Drawings

SUBSTITUTED N-BENZYLPIPERIDINE AMIDES

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are Class III antiarrhythmic agents which, by effectively prolonging repolarization of a cardiac cell action potential, can be used effectively to treat certain cardiac arrhythmias.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta adrenergic blockers, Class III antiarrhythmic agents prolong repolarization, and Class IV antiarrhythmic agents are calcium channel blockers.

Currently, there are very few Class III antiarrhythmic agents available for therapeutic use. Among them is bretylium. Bretylium's usefulness is limited, however, and currently its theraputic use is reserved for life-threatening ventricular arrhythmias that are refractory to other therapy. Thus, bretylium's use is generally confined to intensive care units. It is an object of this invention to provide Class III antiarrhythmic agents of broader theraputic use than existing Class III antiarrhythmic agents.

SUMMARY OF THE INVENTION

The invention relates to novel compounds of the general formula I:

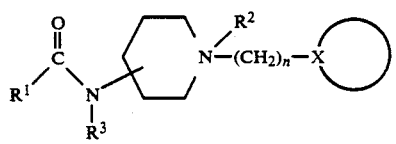

the pharmaceutically acceptable non toxic salts thereof and the hydrated forms thereof,
wherein $R^1$ is alkyl, alkenyl or alkynyl of from one to ten carbon atoms; substituted or unsubstituted aralkyl, aralkenyl or aralkynyl of from one to ten carbon atoms and wherein said aryl substituent is one or more of alkoxy, nitro, halogen or alkylsulfonamide at any position with alkoxy or alkylsulfonamide having alkyl, alkenyl or alkynyl of one to ten carbon atoms; alkyl, alkenyl or alkynyl of from one to ten carbon atoms substituted by furanyl, imidazolyl, pyridinyl, or imidazolyl substituted by alkoxycarbonyl having alkyl, alkenyl or alkynyl of one to ten carbon atoms; arylamino; substituted aryl, unsubstituted aryl or either of them fused to substituted or unsubstituted cycloalkyl of from three to eight carbon atoms wherein said cycloalkyl substituent can be halogen; unsubstituted cycloalkyl of from three to eight carbon atoms arylcycloalkyl wherein cycloalkyl is from three to eight carbon atoms; pyridinyl; furanyl; halogen substituted furanyl; substituted or unsubstituted benzofuranyl wherein said benzofuranyl substituent can be one or more at any position of halogen, amino, nitro or alkoxy having alkyl, alkenyl or alkynyl of from one to ten carbon atoms; substituted or unsubstituted benzopyranyl wherein said substituent can be keto; thiophene; benzothiophene; or substituted or unsubstituted indene or isoindene wherein said substituent is alkyl of one to ten carbon atoms;

n is an integer of from one to ten;

$R^2$ is unsubstituted or is alkyl, alkenyl or alkynyl of from one to ten carbon atoms or oxygen that is present as an N-oxide; $R^3$ is hydrogen, carboxyalkyl, carboxy alkenyl or carboxy alkynyl of from one to ten carbon atoms or alkoxycarbonylalkyl, alkoxycarbonylalkenyl or alkoxycarbonylalkynyl and wherein the alkoxy moiety can have alkyl, alkenyl or alkynyl of from one to ten carbon atoms;

is hydrogen; pyridinyl; cycloalkyl of three to eight carbon atoms or hydroxy substituted cycloalkyl of three to eight carbon atoms; furanyl; or unsubstituted or substituted phenyl wherein said phenyl substituent is one or more of alkyl or halogen substituted alkyl of one to ten carbon atoms, alkoxy from one to ten carbon atoms, nitro, amine, mono or di alkylamine, acetyl amine, acetylamide, halogen or alkoxy itself substituted by halogen substituted phenyl; and $R^4$ is alkoxycarbonyl of from one to ten carbon atoms.

The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

As used herein, the term "alkyl" shall mean straight or branched chain carbon-carbon linkages of from one to ten carbon atoms. "Alkenyl" shall have the same meaning, except that one or more double bonds may be present therein. "Alkynyl" shall have the same meaning, except that one or more triple bonds may be present therein.

"Alkoxy" shall include alkyl, alkenyl and alkynyl, as defined above, substituted by an epoxide oxygen.

"Aralkyl" shall include alkyl, alkenyl and alkynyl, as defined above, substituted by an aryl group, which is defined below.

"Aryl" shall mean phenyl.

"Halogen" shall include fluorine, chlorine, bromine or iodine.

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydroiodic, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate, methaneperoxoate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail. $R^1$, $R^2$, $R^3$ and $$X\bigcirc$$

are as defined above. Y is any suitable leaving group, such as halogen, mesylate or tosylate. COZ represents a suitable acylating agent such as a carboxylic acid chloride, a carboxylic acid activated as the mixed anydride, or the carboxylic ester activated by alkylaluminum reagents.

Scheme 1

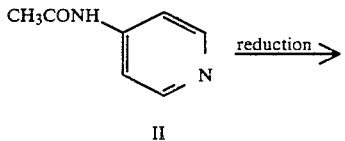
II

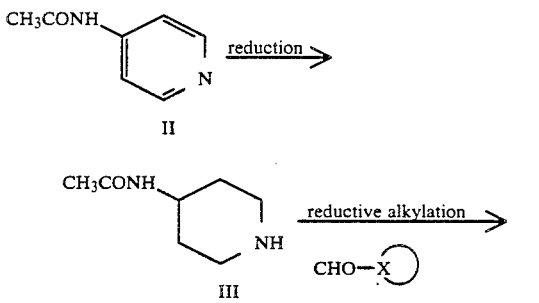
IV
(Where m = n − 1)

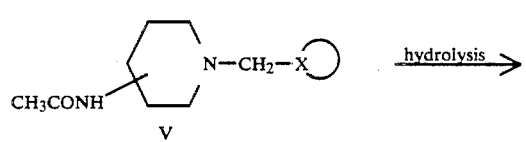
V

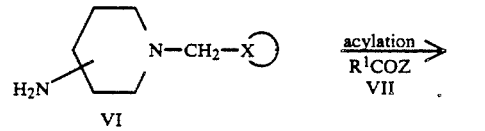
VI

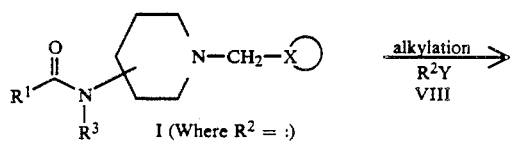
I (Where $R^2$ = :)

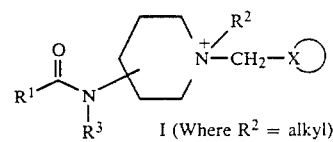
I (Where $R^2$ = alkyl)

Scheme II

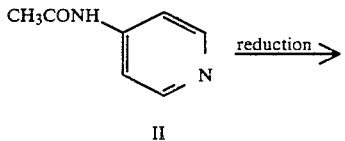
II

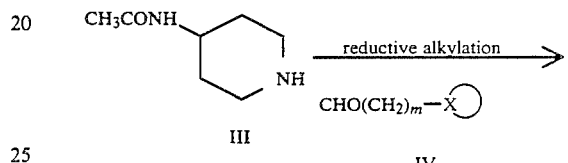
III

IV
(Where m = n − 1)

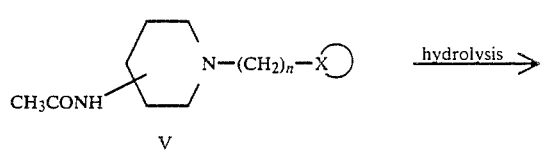
V

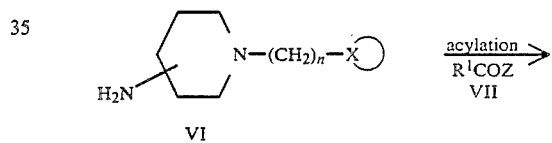
VI

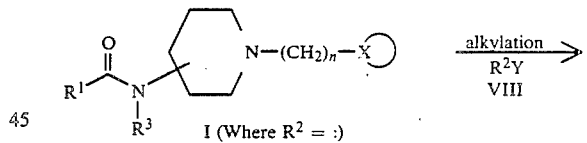
VII

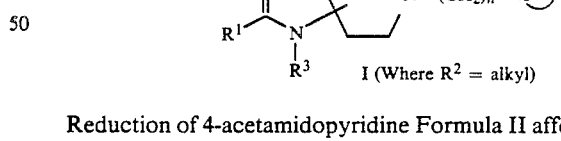
I (Where $R^2$ = :)

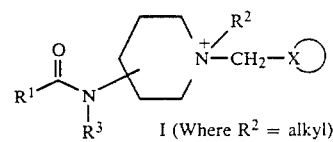
I (Where $R^2$ = alkyl)

Reduction of 4-acetamidopyridine Formula II affords 4-acetamido-piperidine Formula III. A method for the preparation of 4-acetamidopiperidine III involves the reduction of 4-acylamino N-benzyl pyridinium compounds by alkali metal hydrides or catalytic hydrogenation of the aromatic ring with debenzylation as described in U.K. 1,537,867 (G. O. Weston) and U.K. 1,345,872 (J. L. Archibald and J. F. Cavalla) the disclosures of which are incorporated herein by reference. Preferred reduction conditions employ a ruthenium on carbon catalyst in a solvent such as alcohol, tetra hydrofuran, (THF), or acetic acid under an atmosphere of hydrogen. Subsequent reductive alkylation of the piperidine Formula III with aldehydes Formula IV provides the N-alkylated intermediates Formula V. Preferred conditions employ Pt/C catalyst in an inert solvent such as alcohol, THF, or acetic acid under an atmosphere of hydrogen. Alternative preferred conditions employ borane-pyridine complex as the reducing agent at room temperature in alcohol, acetic acid or methylene chloride. Hydrolysis of the amide bond of acetamides Formula V provides amine intermediates Formula VI. Although hydrolysis may be effected in acid or base, the preferred method employs hydrolysis in 1.2 M HCl at 100° C. Alternative preferred acylating conditions leading to amides I ($R^2$=lone pair) employ COZ, which can be a carboxylic acid chloride, a carboxylic acid activated as the mixed anhydride, or the carboxylic ester activated by alkylaluminum reagents.

The intermediates Formula I are subsequently converted to the quaternary salts Formula I (where $R^2$ is not an unshared valence bond) by N-alkylating reagents $R^2X$ Formula VIII (where X is a suitable leaving group such as halogen, mesylate, or tosylate) in an inert solvent. Preferred alkylation conditions employ acetonitrile as the solvent at room temperature.

The compounds of the present invention can be administered in such oral dosage forms as tablets, capsules, pills, powders, granules, elixers, tinctures, suspensions, syrups and emulsions. Likewise, it can also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of arrhythmias of the heart. The dosage regimen utilizing the compound of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.1 mg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below will form the active ingredient that will typically be administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of tablets or capsules, the active drug component can be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components can be combined with any oral non-toxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like.

The compounds of this invention can also be administered by intravenous route in doses ranging from 0.01 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrythmic activity useful in the treatment of various cardiac arrhythmias. The test procedures employed to measure this activity of the compounds of the present invention are described below.

EXAMPLE 1

Guinea pigs, of either sex weighing between 200-350 g, are acutely sacrificed and the right ventricular papillary muscle is isolated. A sample of a given test compound is added using an in vitro tissue bath. Concentrations used are generally $3 \times 10^{-5}$M, but may also be as low as $3 \times 10^{-7}$M. Changes in refractory period are measured before and after adding 1 concentration (usually $3 \times 10^{-5}$M, as noted above) of a test compound to the bath. One hour is allowed for drug equilibration. A compound is considered active (Class III) if an increase in ventricular refractory period is 25 msec or more (at $3 \times 10^{-5}$M).

| Compound | Results Concentration (M) | Change (msec) |
| --- | --- | --- |
| H$_2$O | — | 8 |
| Disopyramide | $3 \times 10^{-5}$ | 20 |
| Clofinium | $3 \times 10^{-5}$ | 24 |
| Sotalol | $3 \times 10^{-5}$ | 35 |
| Example 9 | $3 \times 10^{-5}$ | 55 |
| Example 10 | $3 \times 10^{-5}$ | 50 |
| Example 11 | $3 \times 10^{-5}$ | 30 |
| Example 12 | $1 \times 10^{-6}$ | 20 |
| Example 13 | $3 \times 10^{-5}$ | 40 |
| Example 14 | $1 \times 10^{-6}$ | 15 |
| Example 15 | $3 \times 10^{-5}$ | 40 |
| Example 16 | $1 \times 10^{-6}$ | 30 |
| Example 17 | $3 \times 10^{-5}$ | 30 |
| Example 18 | $3 \times 10^{-5}$ | 55 |
| Example 19 | $1 \times 10^{-6}$ | 25 |
| Example 20 | $1 \times 10^{-6}$ | 40 |
| Example 21 | $3 \times 10^{-5}$ | 190 |
| Example 22 | $3 \times 10^{-5}$ | 95 |
| Example 23 | $3 \times 10^{-5}$ | 35 |
| Example 24 | $3 \times 10^{-5}$ | 60 |

-continued

| Compound | Results Concentration (M) | Change (msec) |
|---|---|---|
| Example 25 | $3 \times 10^{-5}$ | 60 |
| Example 26 | $3 \times 10^{-5}$ | 90 |
| Example 29 | $3 \times 10^{-6}$ | 60 |
| Example 87 | $3 \times 10^{-6}$ | 55 |
| Example 30 | $3 \times 10^{-6}$ | 80 |
| Example 36 | $3 \times 10^{-6}$ | 55 |
| Example 37 | $3 \times 10^{-5}$ | 35 |
| Example 39 | $3 \times 10^{-5}$ | 155 |
| Example 40 | $3 \times 10^{-5}$ | 125 |
| Example 41 | $3 \times 10^{-6}$ | 70 |
| Example 42 | $3 \times 10^{-6}$ | 60 |
| Example 44 | $3 \times 10^{-6}$ | 40 |
| Example 46 | $3 \times 10^{-6}$ | 95 |
| Example 51 | $3 \times 10^{-6}$ | 75 |
| Example 53 | $3 \times 10^{-6}$ | 50 |
| Example 58 | $3 \times 10^{-6}$ | 60 |
| Example 59 | $3 \times 10^{-6}$ | 35 |
| Example 60 | $3 \times 10^{-6}$ | 25 |

-continued

| Compound | Results Concentration (M) | Change (msec) |
|---|---|---|
| Example 64 | $3 \times 10^{-5}$ | 85 |
| Example 66 | $3 \times 10^{-5}$ | 45 |
| Example 69 | $3 \times 10^{-5}$ | 25 |
| Example 70 | $3 \times 10^{-5}$ | 40 |
| Example 72 | $3 \times 10^{-5}$ | 50 |
| Example 75 | $3 \times 10^{-5}$ | 60 |
| Example 77 | $1 \times 10^{-6}$ | 60 |
| Example 78 | $3 \times 10^{-6}$ | 50 |
| Example 80 | $3 \times 10^{-5}$ | 115 |
| Example 82 | $3 \times 10^{-6}$ | 55 |

The preferred compounds of the invention are any or all of those specifically set forth below. The compounds are not, however, to be construed as forming the only genus that is considered as the invention and any combination of such compounds may itself form a genus or sub-genus.

N-[1-(4-pyridinylmethyl)-4-piperidinyl]acetamide

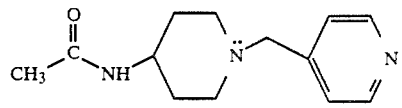

N-[1-[(4-methoxyphenyl)methyl]-4-piperidinyl]acetamide

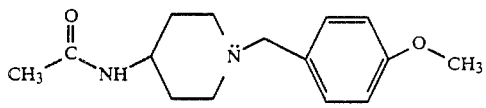

N-[1-[(3-methoxyphenyl)methyl]-4-piperidinyl]acetamide

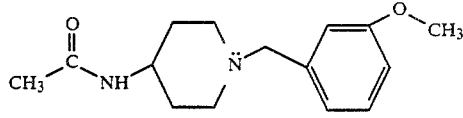

N-[1-[(4-methoxyphenyl)methyl]-4-piperidinyl]acetamide

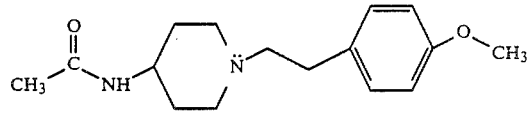

N-[1-[(4-nitrophenyl)methyl]-4-piperidinyl]acetamide

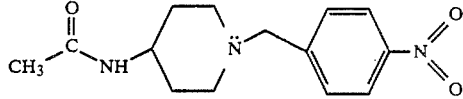

N-[1-[(4-chlorophenyl)methyl]-4-piperidinyl]acetamide

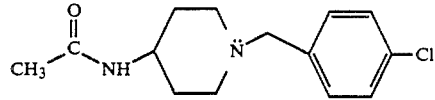

N-[1-[[4-(acetylamino)phenyl]methyl]-4-piperidinyl]acetamide, methaneperoxoate salt

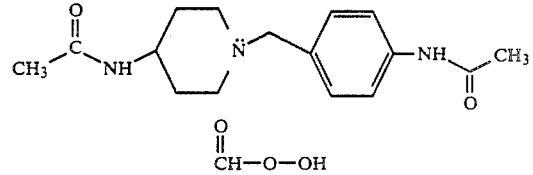

N-[1-[[4-methoxyphenyl)methyl]-3-piperidinyl]acetamide

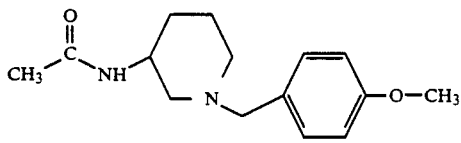

N-[1-(3-furanylmethyl)-4-piperidinyl]acetamide

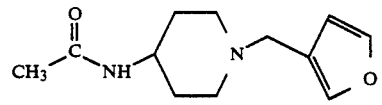

N-[1-[(4-methoxyphenyl)methyl]-4-piperidinyl]2E buteneamide

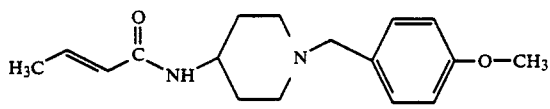

N-[1-[(4-methoxyphenyl)methyl]-4-piperidinyl]benzeneacetamide

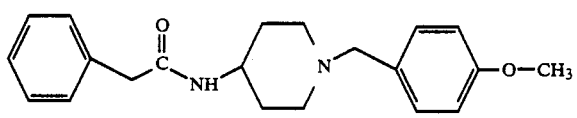

N-[1-[(4-methoxyphenyl)methyl]-4-piperidinyl]benzenepropanamide

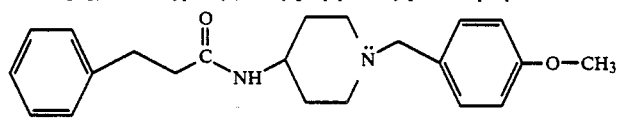

N-[1-[(4-methoxyphenyl)methyl]-4-piperidinyl]benzenebutanamide

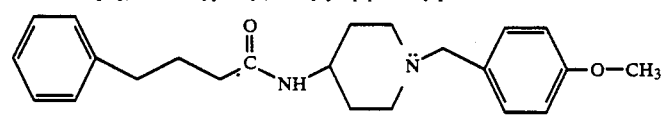

N-[1-[(4-methoxyphenyl)methyl]-4-piperidinyl]-3-phenyl-2E-propenamide

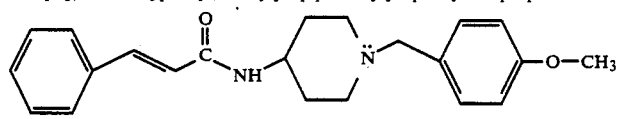

3-phenyl-N-[1-[(propoxyphenyl)methyl]-4-piperidinyl]-2E-propenamide

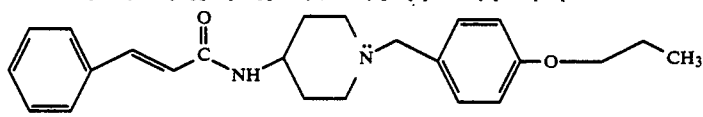

3-(2-methoxyphenyl)-N-[1-[(4-methoxyphenyl)methyl]-4-piperidinyl]-2Z-propenamide

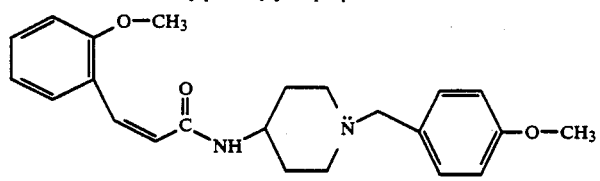

3-(2-methoxyphenyl)-N-[1-[(4-methoxyphenyl)methyl]-4-piperidinyl-2Z-propenamide, monohydrochloride HCl 3-(4-methoxyphenyl)-N-[1-[(4-methoxyphenyl)methyl]-4-piperidinyl]-2E-propenamide

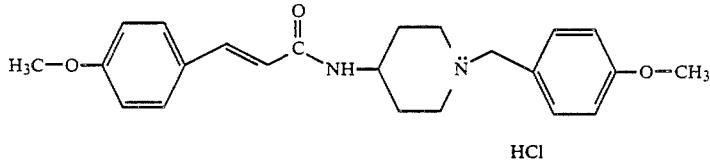

HCl

N-[1-[(4-methoxyphenyl)methyl]-4-piperidinyl]-3-(4-nitrophenyl)-2E-propenamide

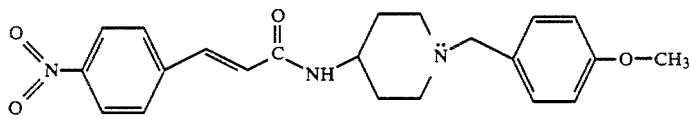

N-[1-[(4-methoxyphenyl)methyl]-4-piperidinyl]-3-[4-[(methylsulfonyl)amino]phenyl]-2E-propenamide

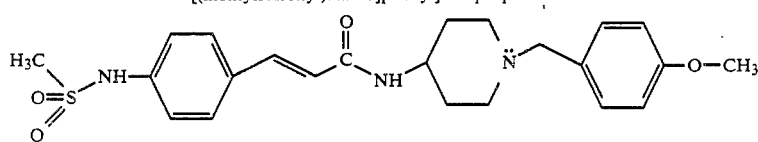

3-(2,6-dichlorophenyl)-N-[1-[(4-methoxyphenyl)methyl]-4-piperidinyl]-2E-propenamide

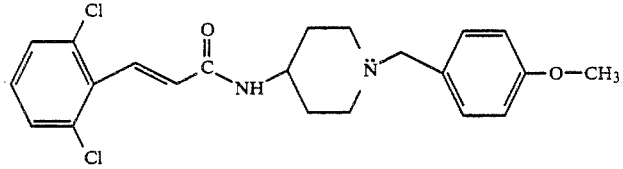

3-(2-furanyl)-N-[1-[(4-methoxyphenyl)methyl]-4-piperidinyl]-2E-propenamide

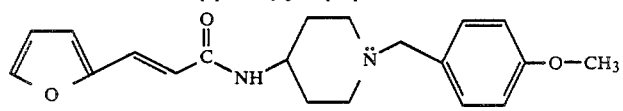

3-(1H-imidazol-4-yl)-N-[(4-methoxyphenyl)methyl]-4-piperidinyl]-2E-propenamide

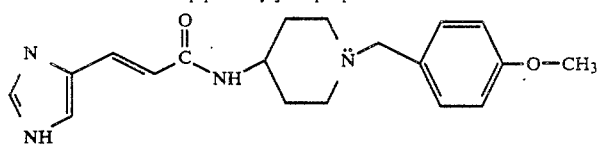

2-methylpropyl 4-[3-[[1-[(4-methoxyphenyl)methyl]-4-piperidinyl]amino]-3-oxo-1E-propenyl]-1H-imidazole-1-carboxylate

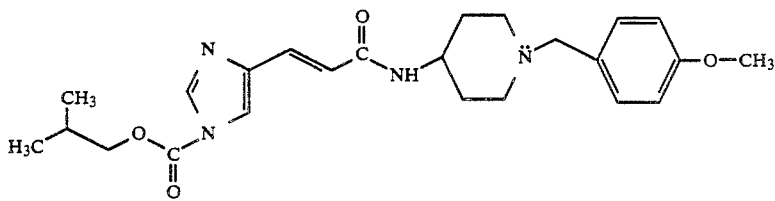

N-[1-[(4-methoxyphenyl)methyl]-4-piperidinyl]-3-(3-pyridinyl)-2E-propenamide

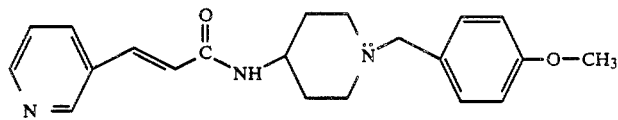

N-[1-[(4-methoxyphenyl)methyl]-4-piperidinyl]-3-phenyl-2-propynamide, monohydrochloride -continued

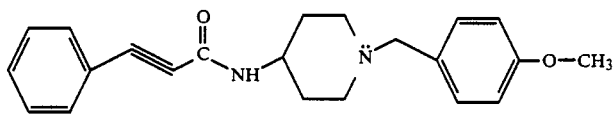

N-phenyl-N'-[1-(phenylmethyl)-4-piperidinyl]urea

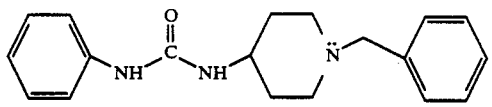

N-[1-[(4-methoxyphenyl)methyl]-4-piperidinyl]-N'-phenylurea

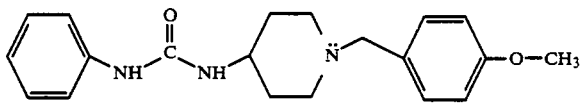

N-[1-[(4-methoxyphenyl)methyl]-4-piperidinyl]-2-phenylcyclopropanecarboxamide

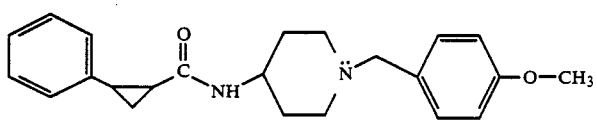

2,3-dihydro-N-[1-[(4-methoxyphenyl)methyl]-4-piperidinyl]-1H-indene-1-carboxamide

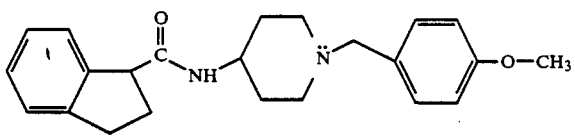

N-[1-[(4-methoxyphenyl)methyl]-4-piperidinyl]-3-methyl-1H-indene-2-carboxamide

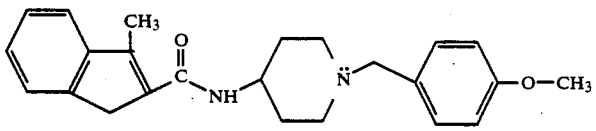

N-[1-(phenylmethyl)-4-piperidinyl]cyclohexanecarboxamide

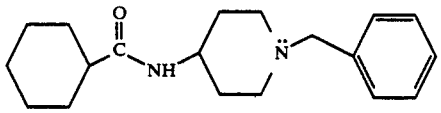

N-[1-[(4-methoxyphenyl)methyl]-4-piperidinyl]cyclohexanecarboxamide

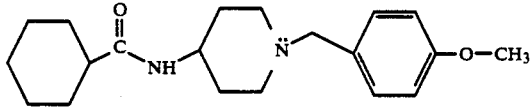

N-[1-[4-[(4-chlorophenyl)methoxy]phenyl]-4-piperidinyl]cyclohexanecarboxamide

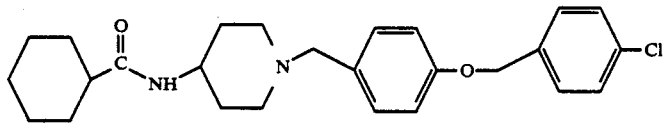

1,2,3,4-tetrahydro-N-[1-[(4-methoxyphenyl)methyl]-4-piperidinyl]-2-naphthalenecarboxamide

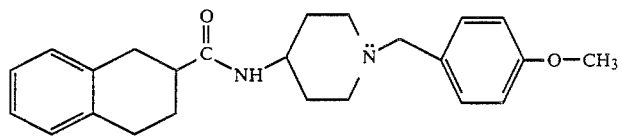

(−)1,2,3,4-tetrahydro-N-[1-[(4-methoxyphenyl)methyl]-
4-piperidinyl]-2-naphthalenecarboxamide

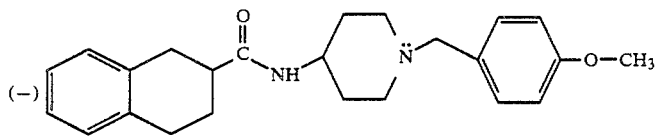

(+)1,2,3,4-tetrahydro-N-[1-[(4-methoxyphenyl)methyl]-
4-piperidinyl]-2-naphthalenecarboxamide

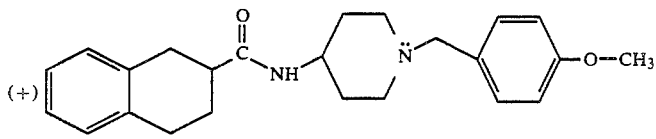

N-[1-[(4-trimethylfluoromethyl)methyl]-4-piperidinyl]
benzamide

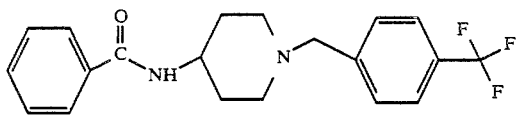

2-methoxy-N-[1-[(4-methoxy)methyl]-4-piperidinyl]benzamide

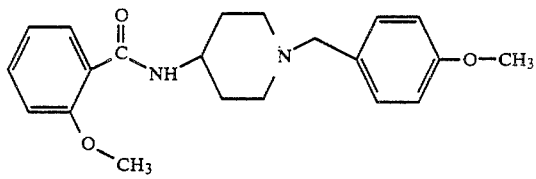

N-[1-(phenylmethyl)-4-piperidinyl]-2-pyridinecarboxamide

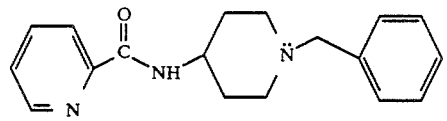

N-[1-(phenylmethyl)-4-piperidinyl]-3-pyridinecarboxamide

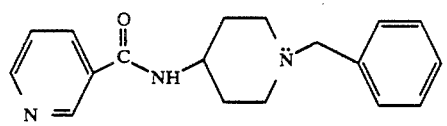

N-[1-(phenylmethyl)-4-piperidinyl]-4-pyridinecarboxamide

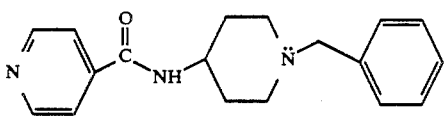

1-[(4-methoxyphenyl)methyl]-N-(3-pyridinyl)-4-
piperidinecarboxamide

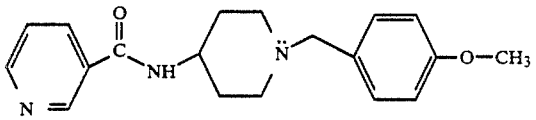

N-[1-(phenylmethyl)-4-piperidinyl]-2-furancarboxamide

-continued

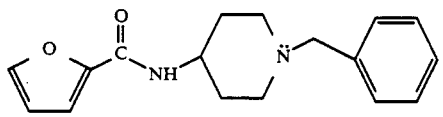
1-[(4-methoxyphenyl)methyl]-N-(2-furanyl)-4-piperidine
carboxamide

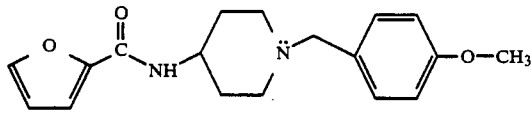
N-[1-[(4-methoxyphenyl)methyl]-4-piperidinyl]-3-
furancarboxamide

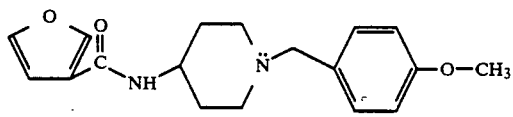
N-[1-[(4-propoxyphenyl)methyl]-4-piperidinyl]-2-
furancarboxamide

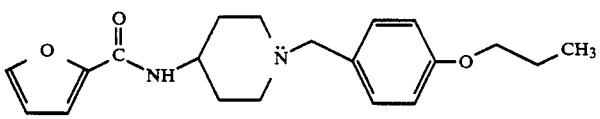
5-bromo-N-[1-[(4-methoxyphenyl)methyl]-4-piperidinyl]-2-
furancarboxamide

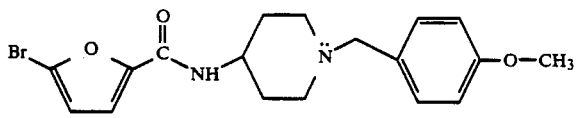
2,3-dihydro-N-[1-[(4-methoxyphenyl)methyl]-4-piperidinyl]-
2-benzofurancarboxamide

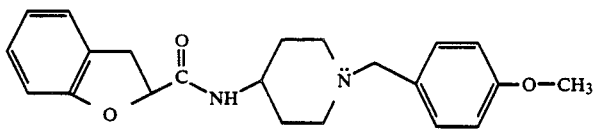
N-(1-methyl-4-piperidinyl)-2-benzofurancarboxamide

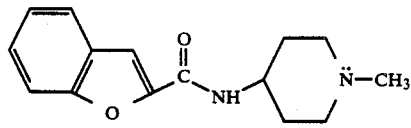
N-(1-(cyclohexylmethyl)-4-piperidinyl]-2-benzofurancarboxamide

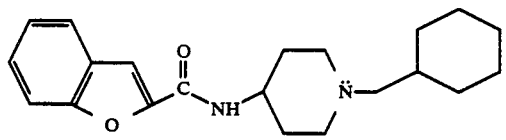
N-[1-(phenylmethyl)-4-piperidinyl]-2-benzofurancarboxamide

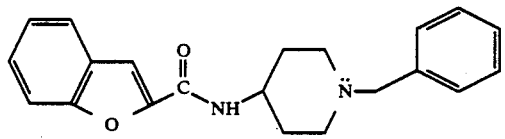
N-[1-[(4-chlorophenyl)methyl]-4-piperidinyl)-2-benzofurancarboxamide

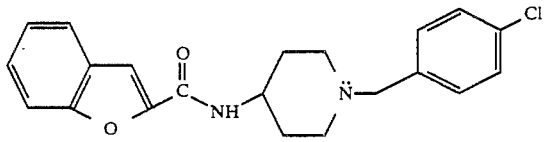

N-[1-[(4-hydroxyphenyl)methyl]-4-piperidinyl]-2-benzofurancarboxamide

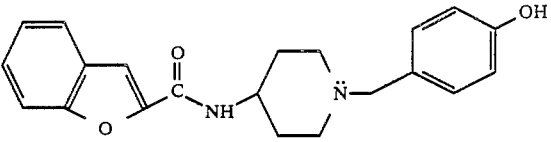

N-[1-[(4-methoxyphenyl)methyl]-4-piperidinyl]-2-benzofurancarboxamide

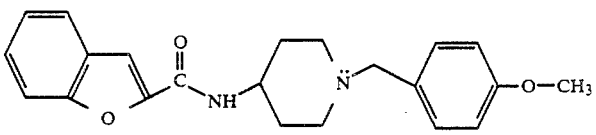

N-[1-[(4-methoxyphenyl)methyl]-4-piperidinyl]-3-benzofurancarboxamide

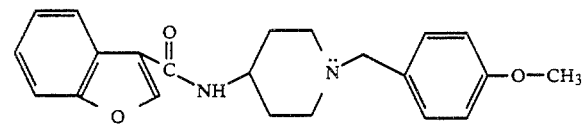

N-[1-[(4-methoxyphenyl)methyl]-3-piperidinyl]-2-benzofurancarboxamide

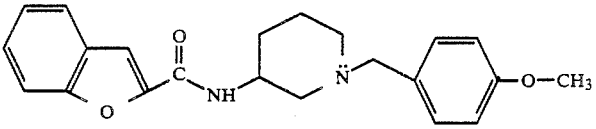

4-[(2-benzofuranylcarbonyl)amino]-1-[(4-methoxyphenyl)methyl]-1-methylpiperidinium iodide

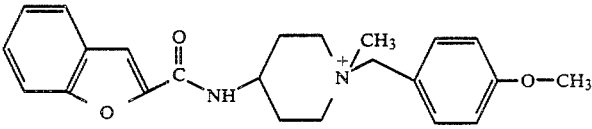

N-[1-[(4-methoxyphenyl)methyl]-4-piperidinyl]-2-benzofurancarboxamide, N-oxide

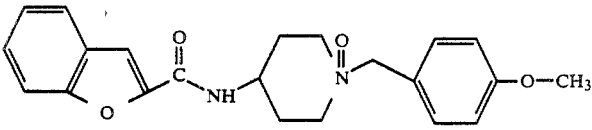

N-[1-[(4-propoxyphenyl)methyl]-4-piperidinyl]-2-benzofurancarboxamide

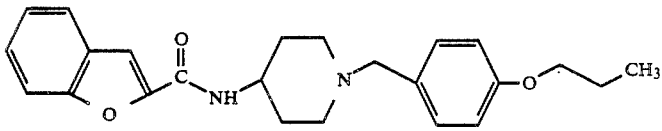

N-[1-[(4-nitrophenyl)methyl]-4-piperidinyl]-2-benzofurancarboxamide

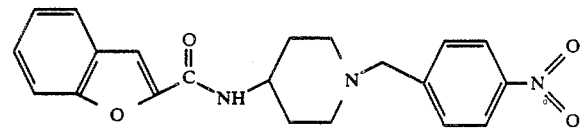

N-[1-[[4-(acetylamino)phenyl]methyl]-4-piperidinyl]-2-benzofurancarboxamide

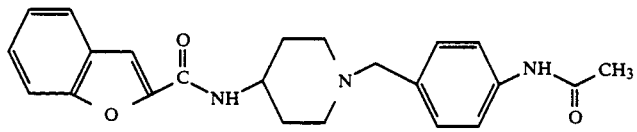

2-methyl-N-[1-[(4-methoxyphenyl)methyl]-4-piperidinyl]-2-benzofurancarboxamide

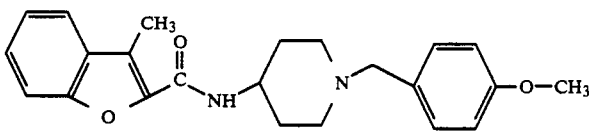

7-chloro-N-[1-[(4-methoxyphenyl)methyl]-4-piperidinyl]-2-benzofurancarboxamide

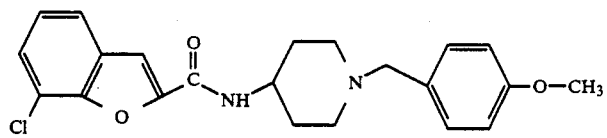

5-chloro-N-[1-[(4-methoxyphenyl)methyl]-4-piperidinyl]-2-benzofurancarboxamide

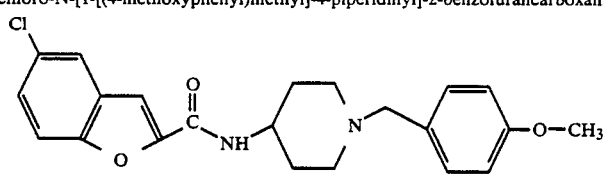

6-amino-N-[1-[(4-methoxyphenyl)methyl]-4-piperidinyl]-2-benzofurancarboxamide

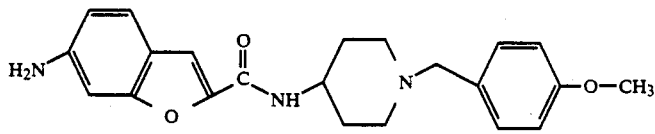

N-[1-[(4-methoxyphenyl)methyl]-4-piperidinyl]-5-nitro-2-benzofurancarboxamide

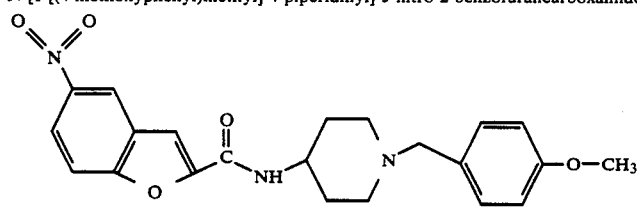

N-[1-[(4-methoxyphenyl)methyl]-4-piperidinyl]-6-nitro-2-benzofurancarboxamide

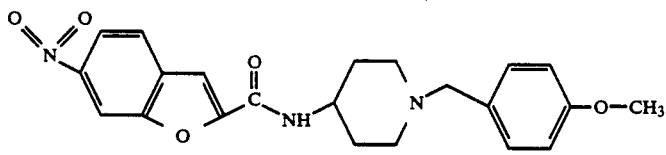

N-[1-[(3-methoxyphenyl)methyl]-4-piperidinyl]-2-benzofurancarboxamide

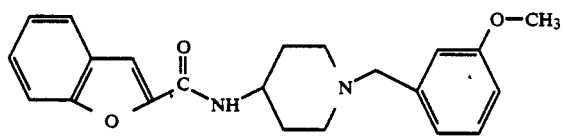

N-[1-[(2,4-dimethoxyphenyl)methyl]-4-piperidinyl]-2-benzofurancarboxamide

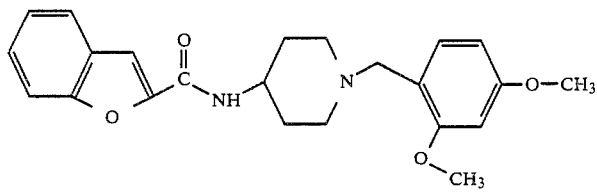

N-[1-[(4-N,N-dimethylaminophenyl)methyl]-4-piperidinyl]-2-
benzofurancarboxamide

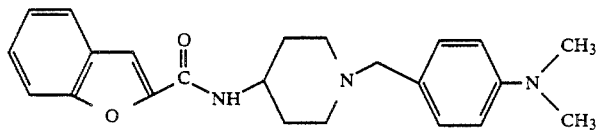

N-[1-[(4-methoxyphenyl)methyl]-4-piperidinyl]-6-nitro-2-
benzofurancarboxamide

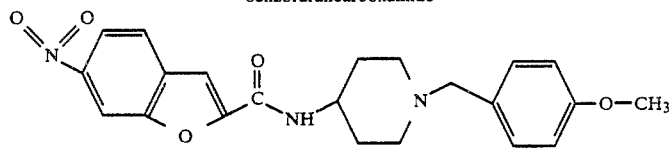

N-[1-[(3-methoxyphenyl)methyl]-4-piperidinyl]-2-
benzofurancarboxamide

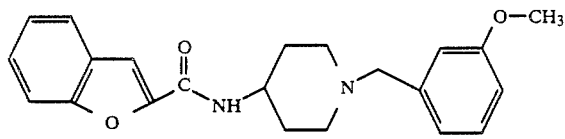

N-[1-[(2,4-dimethoxyphenyl)methyl]-4-piperidinyl]-2-
benzofurancarboxamide

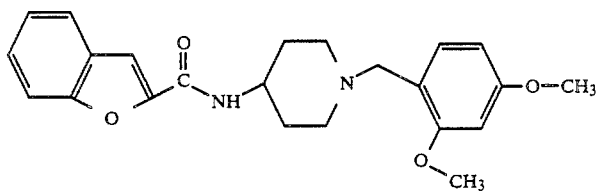

N-[1-[(4-N,N-dimethylaminophenyl)methyl]-4-piperidinyl]-2-
benzofurancarboxamide

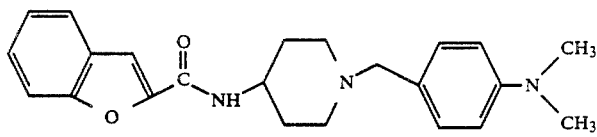

7-methoxy-N-[1-[(4-methoxyphenyl)methyl]-4-piperidinyl]-2-
benzofurancarboxamide, monohydrochloride

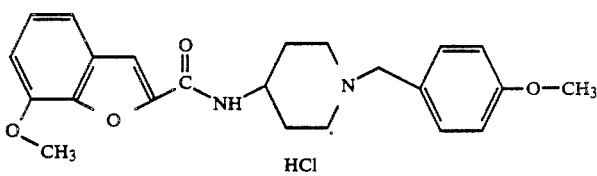

6,7-dimethoxy-N-[1-[(4-methoxyphenyl)methyl]-4-piperidinyl]-2-
benzofurancarboxamide

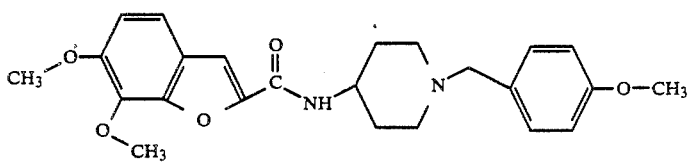

-continued

N-[1-[(4-methoxyphenyl)methyl]-4-piperidinyl]-2-oxo-2H-1-benzopyran-3-carboxamide

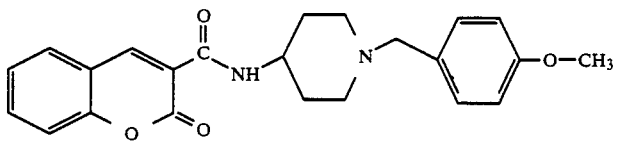

N-[1-[(4-methoxyphenyl)methyl]-4-piperidinyl]-4-oxo-4H-1-benzopyran-3-carboxamide, monohydrochloride

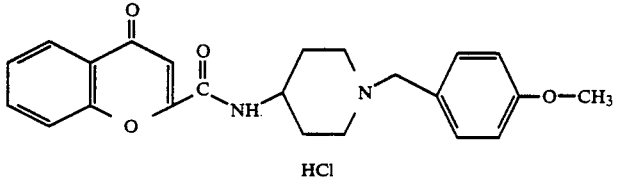

N-[1-[(4-methoxyphenyl)methyl]-4-piperidinyl]-2-thiophenecarboxamide

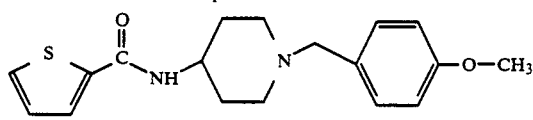

N-[1-[(4-methoxyphenyl)methyl]-4-piperidinyl]-2-benzo[b]thiophenecarboxamide

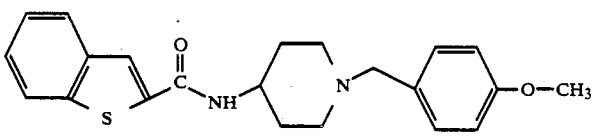

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt Capillary Apparatus and are not corrected. Unless otherwise noted, I.R. and NMR spectra were consistent with the assigned structure.

EXAMPLE 2

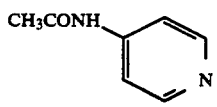

Preparation of 4-acetamidopyridine acetate II

4-Aminopyridine (101.28 g) and acetic anhydride (110 g) were mixed neat and heated at 100° C. for ½ h. The solidified reaction mixture was triturated with acetone, filtered off, and washed with ether to afford 186.48 g of II as a white solid in two crops. Anal. calcd for $C_9H_{12}N_2O_3$: C, 55.09; H, 6.16; N, 14.26. Found: C, 55.04; H, 5.96; N, 15.22.

EXAMPLE 3

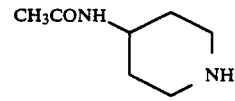

Preparation of 4-acetamidopiperidine acetate III

A solution of the product of Example 2 (75 g) in 750 mL acetic acid was reduced over $PtO_2$ catalyst at 60 psi hydrogen atmosphere at 60° C. for 7 hours. The solution was filtered, concentrated and triturated with ether to afford the title compound quantitatively as a white solid which was used directly in subsequent reactions.

EXAMPLE 4

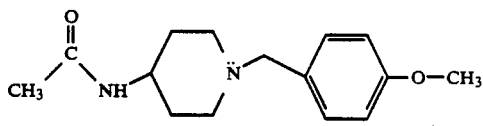

Preparation of 1-(4-methoxyphenyl)methyl-4-acetamido-piperidine

A mixture of 10 g amine acetate from Example 3 and 13.48 g 4-methoxy benzaldehyde was hydrogenated in 100 mL ethanol over a Pt/C catalyst at room temperature for 3 hours. The reaction mixture was filtered and concentrated to give 74.0 g of the acetate salt of the title compound as a white solid which was hydrolyzed directly as described in Example 4. (An alternative reductive amination procedure is described in Example 5). Conversion of a sample to the free base using aqueous base and ethyl acetate extraction provided a white solid after solvent evaporation and trituration with ether: mp 140°–142° C.; Anal. calcd for $C_{15}H_{22}N_2O_2$: C, 68.67; H, 8.45; N, 10.68. Found: C, 65.26; H, 8.60; N, 10.77.

EXAMPLE 5

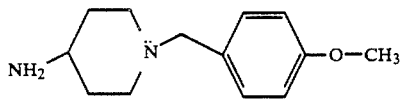

Preparation of 1-(4-methoxyphenyl)methyl-4-amino piperidine

A) A solution of 50 g of the product of Example 4 was dissolved in 500 mL of 1.2N HCl and heated at 100° C. for 8 h. The solution was made alkaline with 50% aq. NaOH and extracted three times with ether. The combined organic layers were washed with water and saturated brine, dried over sodium sulfate, and concentrated to give the title compound as 28 g of clear oil which was used without further purification.

B) (Alternative general reductive alkylation procedure) A solution of 50 mmol amine acetate (product of Example 3) and 100 mmol of 4-methoxybenzaldehyde in 125 mL methylene chloride and 15 mL acetic acid was treated with 50 mmol of borane-pyridine complex and allowed to stir at room temperature overnight. The removal of volatiles by rotary evaporation afforded the acetamide of Example 4 as an oil which was dissolved in 300 mL of 1.2N HCl and heated overnight on a steam bath. The cooled reaction mixture was extracted once with a 50 mL portion of ethyl acetate which was discarded. The aqueous layer was made basic with aq. NaOH and extracted three times with 50 mL ether. The combined layers were washed with water and dried over sodium sulfate. Solvent removal afforded the title compound as a crude oil (yield typically 60–70% for two steps) which was used directly without further purification.

EXAMPLE 6

General acylation procedures

A) 10 mmol of the amine of Example 5 is dissolved in a mixture of 25 mL chloroform and 11 mmol of triethylamine cooled to 0° C. A solution of 11 mmol of the acyl chloride neat or dissolved in 25 mL chloroform is added dropwise and the reaction mixture is allowed to stir for 1 h. Volatiles are removed in vacuo and the residue is partitioned between dilute aqueous base and ethyl acetate. Drying of the ethyl acetate extract and evaporation leads to the crude product which is optionally purified by flash chromatography on silica gel using 92.5:7:0.5 chloroform:ethanol:ammonium hydroxide and crystallized from ethyl acetate/hexane or converted to the HCl salt using dioxane/HCl followed by recrystallization from methanol/ether.

B) A stirred solution of 10 mmol acylating acid in 25 mL chloroform is treated with 10 mmol of triethylamine followed by 10 mmol of isobutyl chloroformate. After 10 minutes at ambient temperature the amine of Example 5 was added and the reaction is allowed to stir for ½ h. The reaction mixture is washed with 10% NaOH solution and the organic layer is dried and evaporated to give a residue which is optionally purified by flash chromatography on silica gel using 92.5:7:0.5 chloroform:ethanol:ammonium hydroxide recrystallized from ethyl acetate converted to the HCl salt using dioxane/HCl followed by recrystallization from methanol/ether.

EXAMPLE 7

Preparation of quaternary salt

A solution of 200 mg of the amide of Example 6 in 5 mL acetone was treated with 4 drops of iodomethane. The reaction mixture was stirred for 18 h and the white crystalline precipitate was filtered off to afford 206 mg of white solid which was recrystallized from acetonitrile to give 128 mg of quaternary iodide as fluffy white needles, mp 236°–237° C.

EXAMPLE 8

Preparation of N-oxide

A solution of 0.50 g of the amide of Example 6 in 10 mL $CH_2Cl_2$ was treated with 300 mg of m-chloroperoxybenzoic acid at 0° C. After 1 h the solution was washed consecutively with 10 mL 1N NaOH, water, and sat'd. brine. The solution was dried over sodium sulfate and concentrated to afford 0.51 g of white solid which was recrystallized from $CH_2Cl_2$/ethyl acetate to give 0.33 g of an N-oxide as a white powder, mp 200.5°–202.5° C.

EXAMPLE 9 THROUGH 89

Using the procedures of Examples 2 through 8 and making the appropriate substitutions at positions $R_1$, $R_2$, $R_3$, and X, the following products were obtained as presented in Table I, below. Table I specifies the moiety at $R_1$, $R_2$, $R_3$ and

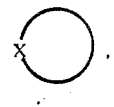

the number of methylenes represented by n, the compound's melting point range in degrees Celsius (where available) and the compound's elemental analysis.

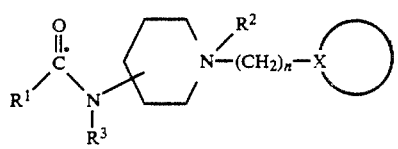

All piperidinyls are 4-piperidinyl unless otherwise noted.

| Example | R¹ | R² | R³ | X | n | mp, deg. C. | Analysis |
|---|---|---|---|---|---|---|---|
| 9 | 4-pyridyl | | H | phenyl | 1 | | $C_{18}H_{21}N_3O$ |
| 10 | 3-pyridyl | | H | phenyl | 1 | | $C_{18}H_{21}N_3O$ |
| 11 | 2-pyridyl | | H | phenyl | 1 | | $C_{18}H_{21}N_3O$ |
| 12 | cyclohexyl | | H | 4-(4-chlorobenzyloxy)phenyl | 1 | | $C_{26}H_{33}ClN_2O_2$ |
| 13 | cyclohexyl | | H | phenyl | 1 | 155–157 | $C_{19}H_{28}N_2O$ |
| 14 | 2-(phenylamino) | | H | phenyl | 1 | 168–169.5 | $C_{19}H_{23}N_3O$ |
| 15 | 2-furyl | | H | phenyl | 1 | 155.5–158 | $C_{17}H_{20}N_2O_2$ |
| 16 | cyclohexyl | | H | 4-methoxyphenyl | 1 | 170–171 | $C_{20}H_{30}N_2O_2$ |

-continued

| Example | R¹ | R² | R³ | X | n | mp, deg. C. | Analysis |
|---------|----|----|----|---|---|-------------|----------|
| 17 | —CH₃ | | H | 4-methoxyphenyl | 1 | 137–140 | $C_{15}H_{22}N_2O_2$ |
| 18 | 2-furyl | | H | 4-methoxyphenyl | 1 | 136–137 | $C_{18}H_{22}N_2O_3$ |
| 19 | cyclopropylphenyl | | H | 4-methoxyphenyl | 1 | 142–143 | $C_{23}H_{28}N_2O_2$ |
| 20 | styryl (trans-cinnamyl) | | H | 4-methoxyphenyl | 1 | 135–137 | $C_{22}H_{26}N_2O_2$ |
| 21 | 2-methylbenzofuran-3-yl | | H | 4-methoxyphenyl | 1 | 136–138 | $C_{22}H_{24}N_2O_3$ |
| 22 | 4-methylpyridin-3-yl | | H | 4-methoxyphenyl | 1 | — | $C_{19}H_{23}N_3O_2$ |
| 23 | 2-methylthien-3-yl | | H | 4-methoxyphenyl | 1 | 161–162 | $C_{18}H_{22}N_2O_2S$ |
| 24 | 3-methylcoumarin-4-yl | | H | 4-methoxyphenyl | 1 | 200–202 | $C_{23}H_{24}N_2O_4$ |

-continued

| Example | R¹ | R² | R³ | X | n | mp. deg. C. | Analysis |
|---|---|---|---|---|---|---|---|
| 25 | [imidazole with propenyl] | | H | [4-methoxyphenyl] | 1 | 210–211 | $C_{19}H_{24}N_2O_2$ |
| 26 | [imidazole-N-C(O)O-CH₂CH(CH₃)₂ with propenyl] | | H | [4-methoxyphenyl] | 1 | 134–137 | $C_{24}H_{32}N_2O_4$ |
| 27 | CH₃ | | H | [4-methoxyphenyl] | 2 | 162–164 | $C_{16}H_{24}N_2O_2$ |
| 28 | [furan] | | H | [4-methoxyphenyl] | 1 | 178.5–179.5 | $C_{18}H_{22}N_2O_2$ |
| 29 | [benzofuran] | | H | [4-methoxyphenyl] | 1 | 140–141 | $C_{22}H_{24}N_2O_3$ |
| 30 | [methylindene] | | H | [4-methoxyphenyl] | 1 | 135–137 | $C_{23}H_{28}N_2O_2$ |
| 31 | [styryl] | | H | [4-(O(CH₂)₂CH₃)phenyl] | 1 | 156–158 | $C_{24}H_{30}N_2O_2$ |

-continued

| Example | R¹ | R² | R³ | X | n | mp, deg. C. | Analysis |
|---|---|---|---|---|---|---|---|
| 32 | 5-methylfuran-2-yl | | H | 4-(O-(CH₂)₂CH₃)-phenyl | 1 | 122-124 | $C_{20}H_{26}N_2O_3$ |
| 33 | 2-methylbenzofuran-3-yl | | H | 4-(O-(CH₂)₂CH₃)-phenyl | 1 | 132-134 | $C_{24}H_{28}N_2O_3$ |
| 34 | 2-methyl-5-chlorobenzofuran-3-yl | | H | 4-OCH₃-phenyl | 1 | 148-149 | $C_{22}H_{23}ClN_2O_3$ |
| 35 | 3-methylbenzofuran-2-yl | | H | 4-OCH₃-phenyl | 1 | 156-158 | $C_{23}H_{26}N_2O_2$ |
| 36 | 2-methyl-7-methoxybenzofuran-3-yl | | H | 4-OCH₃-phenyl | 1 | 140-142 | $C_{23}H_{26}N_2O_4 \cdot HCl$ |
| 37 | 2-methyl-6,7-dimethoxybenzofuran-3-yl | | H | 4-OCH₃-phenyl | 1 | 147-148 | $C_{24}H_{28}N_2O_5$ |
| 38 | 2-methyl-7-chlorobenzofuran-3-yl | | H | 4-OCH₃-phenyl | 1 | 126-128 | $C_{22}H_{23}ClN_2O_3$ |

-continued

| Example | R¹ | R² | R³ | X | n | mp, deg. C. | Analysis |
|---|---|---|---|---|---|---|---|
| 39 | 2-methylbenzothiophen-3-yl | | H | 4-methoxyphenyl | 1 | 158–160 | $C_{22}H_{24}N_2O_2S$ |
| 40 | 3-methyl-4-oxo-4H-chromen-2-yl | | H | 4-methoxyphenyl | 1 | 270–272 | $C_{23}H_{24}N_2O_4 \cdot HCl$ |
| 41 | phenylethynyl | | H | 4-methoxyphenyl | 1 | oil | $C_{22}H_{25}N_2O_2 \cdot HCl$ |
| 42 | 2-furylvinyl | | H | 4-methoxyphenyl | 1 | 146–148 | $C_{23}H_{28}N_2O_3$ |
| 43 | 4-methoxystyryl | | H | 4-methoxyphenyl | 1 | 147–149 | $C_{23}H_{28}N_2O_3$ |
| 44 | phenylamino | | H | 4-methoxyphenyl | 1 | 145–147 | $C_{20}H_{25}N_3O_2$ |
| 45 | 2-(pyridin-3-yl)vinyl | | H | 4-methoxyphenyl | 1 | 150–152 | $C_{21}H_{25}N_3O_2$ |
| 46 | 2-methyl-3-benzofuranyl | | H | 4-methoxyphenyl | 1 | 142–144 | $C_{23}H_{26}N_2O_3$ |

-continued

| Example | R¹ | R² | R³ | X | n | mp, deg. C. | Analysis |
|---|---|---|---|---|---|---|---|
| 47 | —CH₂CH₂—phenyl | | H | 4-methoxyphenyl | 1 | 131-133 | $C_{22}H_{28}N_2O_2$ |
| 48 | 2-methoxyphenyl-CH=CH— | | H | 4-methoxyphenyl | 1 | 141-143 | $C_{23}H_{28}N_2O_2$ |
| 49 | —CH₂CH₂CH₂—phenyl | | H | 4-methoxyphenyl | 1 | 125-127 | $C_{23}H_{30}N_2O_2 \cdot HCl$ |
| 50 | 2-methoxyphenyl-CH=CH— (cis) | | H | 4-methoxyphenyl | 1 | 92-96 | $C_{23}H_{28}N_2O_2 \cdot HCl$ |
| 51 | 2,3-dihydrobenzofuran-3-yl (±) | | H | 4-methoxyphenyl | 1 | 134.5-135 | $C_{22}H_{26}N_2O_3$ |
| 52 | —CH₂—phenyl | | H | 4-methoxyphenyl | 1 | | $C_{21}H_{26}N_2O_2$ |
| 53 | 2-methyl-5-nitrobenzofuran-yl | | H | 4-methoxyphenyl | 1 | 190-192 | $C_{22}H_{23}N_3O_5$ |
| 54 | 4-nitrophenyl-CH=CH— | | H | 4-methoxyphenyl | 1 | 197-199 | $C_{22}H_{25}N_3O_4$ |

-continued

| Example | R¹ | R² | R³ | X | n | mp, deg. C. | Analysis |
|---|---|---|---|---|---|---|---|
| 55 | CH₃–CH=CH– | | H | 4-methoxyphenyl | 1 | | $C_{17}H_{24}N_2O_2$ |
| 56 | 2,6-dichlorophenyl-propylidene | | H | 4-methoxyphenyl | 1 | 210–212 | $C_{22}H_{24}Cl_2N_2O_2$ |
| 57 | 6-tetrahydronaphthyl (–) | | H | 4-methoxyphenyl | 1 | 142–143 | $C_{24}H_{30}N_2O_2$ |
| 58 | 5-bromo-2-methylfuryl | | H | 4-methoxyphenyl | 1 | 133–135 | $C_{18}H_{21}BrN_2O_3$ |
| 59 | 2-methylbenzofuranyl | | H | phenyl | 1 | 155–157 | $C_{21}H_{22}N_2O_3$ |
| 60 | 4-(methanesulfonamido)cinnamyl | | H | 4-methoxyphenyl | 1 | 215–218 | $C_{23}H_{29}N_3O_4S$ |
| 61 | CH₃ | | H | 4-nitrophenyl | 1 | 143–144 | $C_{14}H_{19}N_3O_3$ |
| 62 | 2-methylbenzofuranyl | | H | 4-nitrophenyl | 1 | 155–157 | $C_{21}H_{21}N_3O_4$ |

-continued

| Example | R¹ | R² | R³ | X | n | mp, deg. C. | Analysis |
|---|---|---|---|---|---|---|---|
| 63 | CH₃ | | H | 4-Cl-phenyl | 1 | 162–164 | $C_{14}H_{19}ClN_2O$ |
| 64 | 2-methylbenzofuran-3-yl | | H | 4-Cl-phenyl | 1 | 137–139 | $C_{21}H_{21}ClN_2O_2$ |
| 65 | 2-methyl-tetrahydronaphthyl (+) | | H | 4-OCH₃-phenyl | 1 | 157–159 | $C_{24}H_{30}N_2O_2$ |
| 66 | 2-methylbenzofuran-3-yl | | H | 4-OCH₃-phenyl | 1 | 236–237 | $C_{23}H_{26}N_2O_3 \cdot HI$ |
| 67 | 2-methylbenzofuran-3-yl | CH₃ | H | cyclohexyl | 1 | 184–185.5 | $C_{21}H_{28}N_2O_2$ |
| 68 | CH₃ | | H | 4-pyridyl | 1 | 163–164.5 | $C_{13}H_{19}N_3O$ |
| 69 | CH₃ | | H | (3-piperidyl) 4-OCH₃-phenyl | 1 | 103–105 | $C_{15}H_{22}N_2O_2$ |
| 70 | 2-methylbenzofuran-3-yl | | H | (3-piperidyl) 4-OCH₃-phenyl | 1 | 114–115 | $C_{22}H_{24}N_2O_3$ |

-continued

| Example | R¹ | R² | R³ | X | n | mp, deg. C. | Analysis |
|---|---|---|---|---|---|---|---|
| 71 | CH₃ | | H | 3-methoxyphenyl | 1 | | $C_{15}H_{22}N_2O_2$ |
| 72 | 2-methylbenzofuran-3-yl | O | H | 4-methoxyphenyl | 1 | 200.5–202.5 | $C_{22}H_{24}N_2O_4$ |
| 73 | CH₃ | | H | H | 1 | | $C_{15}H_{18}N_2O_2$ |
| 74 | 2-methylbenzofuran-3-yl | | H | 4-(NHCOCH₃)phenyl | 1 | 145–147 | $C_{16}H_{23}N_3O_2 \cdot CHOOOH$ |
| 75 | 2-methylbenzofuran-3-yl | | H | 4-(NHCOCH₃)phenyl | 1 | 230–232 | $C_{23}H_{25}N_3O_3$ |
| 76 | 2-methylbenzofuran-3-yl | | H | 3-methoxyphenyl | 1 | | $C_{22}H_{25}ClN_2O_3$ |
| 77 | 2-methylbenzofuran-3-yl | | H | 2,5-dimethoxyphenyl | 1 | | $C_{23}H_{26}N_2O_4$ |

-continued

| Example | R¹ | R² | R³ | X | n | mp, deg. C. | Analysis |
|---|---|---|---|---|---|---|---|
| 78 | 2-methylbenzofuran-3-yl | | H | 4-(N,N-dimethylamino)phenyl | 1 | | $C_{23}H_{27}N_3O_2 \cdot 2(HCl)$ |
| 79 | 2-methyl-6-nitrobenzofuran-3-yl | | H | 4-methoxyphenyl | 1 | 189–190 | $C_{22}H_{23}N_3O_5$ |
| 80 | 2-methyl-6-aminobenzofuran-3-yl | | H | 4-methoxyphenyl | 1 | 98–100 | $C_{22}H_{27}N_3O_3 \cdot 2(HCl)$ |
| 81 | $CH_3$ | | H | phenyl (substituted by $CO_2CH_2CH_3$) | 1 | | $C_{17}H_{24}N_2O_3$ |
| 82 | 2-methylbenzofuran-3-yl | | $-CH_2CO_2CH_2CH_3$ | 4-methoxyphenyl | 1 | | $C_{26}H_{31}ClN_2O_5$ |
| 83 | 2-methylbenzofuran-3-yl | | $-CH_2CO_2H$ | 4-methoxyphenyl | 1 | | $C_{24}H_{26}N_2O_5$ |
| 84 | 2-tetrahydronaphthyl (+) | | H | 4-methoxyphenyl | 1 | 152–153 | $C_{24}H_{30}N_2O_2$ |
| 85 | 2-methylbenzofuran-3-yl | | H | 4-hydroxyphenyl | 1 | 198–200 | $C_{21}H_{22}N_2O_3$ |

-continued

| Example | R¹ | R² | R³ | X | n | mp, deg. C. | Analysis |
|---|---|---|---|---|---|---|---|
| 86 | CH₃ | | H | furan-3-yl | 1 | | $C_{12}H_{18}N_2O_2$ |
| 87 | 2,3-dihydro-1H-inden-1-yl | | H | 4-methoxyphenyl | 1 | | $C_{23}H_{28}N_2O_2$ |
| 88 | phenyl | | H | 4-(trifluoromethyl)phenyl | 1 | | $C_{20}H_{22}N_2OF_3$ |
| 89 | 2-methoxyphenyl | | H | 4-methoxyphenyl | 1 | | $C_{21}H_{27}N_2O_3$ |

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations for differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound of the formula

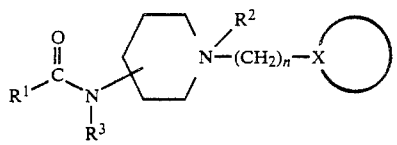

or the pharmaceutically acceptable non-toxic salts thereof, or the hydrated forms thereof, wherein $R^1$ is alkenyl or alkynyl of from two to ten carbon atoms; substituted or unsubstituted phenylalkenyl or phenylalkynyl of from two to ten carbon atoms and wherein said phenyl substituent is one or more of alkoxy, nitro, halogen or alkylsulfonamide at any position with alkoxy or alkylsulfonamide of one to ten carbon atoms; unsubstituted phenyl which is fused to substituted or unsubstituted cycloalkyl of from three to eight carbon atoms wherein said cycloalkyl substituent can be halogen; phenylamino; phenylcycloalkyl wherein cycloalkyl is from three to eight carbon atoms; furanyl alkenyl wherein the alkenyl portion is from two to eight carbon atoms; substituted or unsubstituted benzofuranyl wherein said benzofuranyl substituent can be one or more of halogen, amino, nitro or alkoxy of from one to ten carbon atoms at any position; substituted or unsubstituted benzopyran wherein said substituent can be keto; thiophene; benzothiophene; or substituted or unsubstituted indene or isoindene wherein said substituent is alkyl of one to ten carbon atoms;

n is an integer of from one to ten;

$R^2$ is alkyl of from one to ten carbon atoms, oxygen that is present as an N-oxide or absent; $R^3$ is hydrogen, carboxyalkyl of from one to ten carbon atoms or alkoxycarbonylalkyl of from one to ten carbon atoms;

is hydrogen; pyridinyl; cycloalkyl of three to eight carbon atoms or hydroxy substituted cycloalkyl of three to eight carbon atoms; furanyl; or unsubstituted or substituted phenyl wherein said phenyl substituent is one or more of alkyl or halogen substituted alkyl of one to ten carbon atoms, alkoxy from one to ten carbon atoms, nitro, amine, mono or dialkylamine, acetyl amine, acetylamide, halogen, hydroxy or alkoxy itself substituted by halogen substituted phenyl.

2. The compound as claimed in claim 1, wherein $R^1$ is —CH=CH—CH$_3$.

3. The compound as claimed in claim 1, wherein $R^1$ is

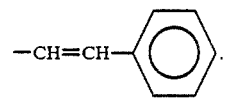

4. The compound as claimed in claim 1, wherein $R^1$ is

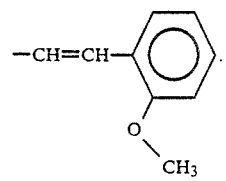

5. The compound as claimed in claim 1, wherein $R^1$ is

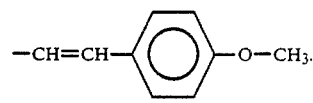

6. The compound as claimed in claim 1, wherein $R^1$ is

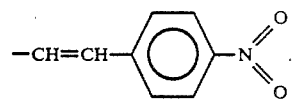

7. The compound as claimed in claim 1, wherein $R^1$ is

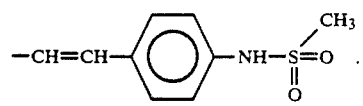

8. The compound as claimed in claim 1, wherein $R^1$ is

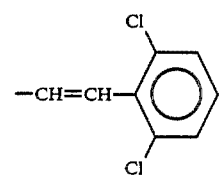

9. The compound as claimed in claim 1, wherein $R^1$ is

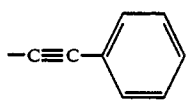

10. The compound as claimed in claim 1, wherein R¹ is

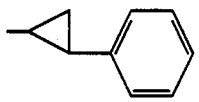

11. The compound as claimed in claim 1, wherein R¹ is

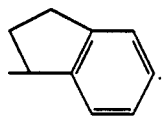

12. The compound as claimed in claim 1, wherein R¹ is

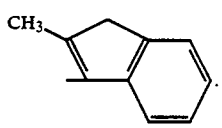

13. The compound as claimed in claim 1, wherein R¹ is

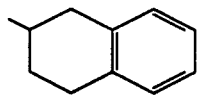

14. The compound as claimed in claim 1, wherein R¹ is

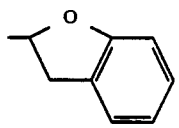

15. The compound as claimed in claim 1, wherein R¹ is

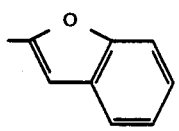

16. The compound as claimed in claim 1, wherein R¹ is

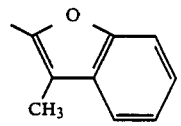

17. The compound as claimed in claim 1, wherein R¹ is

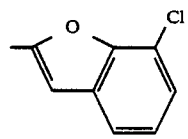

18. The compound as claimed in claim 1, wherein R¹ is

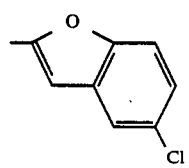

19. The compound as claimed in claim 1, wherein R¹ is

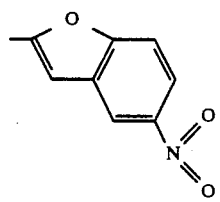

20. The compound as claimed in claim 1, wherein R¹ is

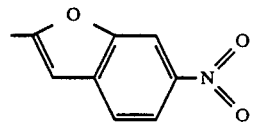

21. The compound as claimed in claim 1, wherein R¹ is

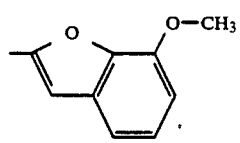

22. The compound as claimed in claim 1, wherein R¹ is

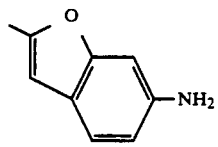

23. The compound as claimed in claim 1, wherein $R^1$ is

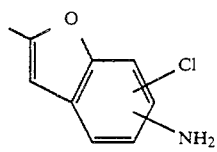

24. The compound as claimed in claim 1, wherein $R^1$ is

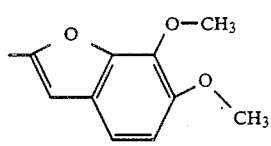

25. The compound as claimed in claim 1, wherein $R^1$ is

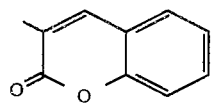

26. The compound as claimed in claim 1, wherein $R^1$ is

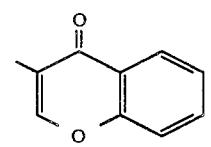

27. The compound as claimed in claim 1, wherein $R^1$ is

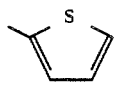

28. The compound as claimed in claim 1, wherein $R^1$ is

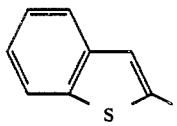

29. The compound as claimed in claim 1, wherein n is 1.

30. The compound as claimed in claim 1, wherein n is 2.

31. The compound as claimed in claim 1, wherein $R^2$ is —$CH_3$.

32. The compound as claimed in claim 1, wherein $R^2$ is oxygen, present as an N-oxide.

33. The compound as claimed in claim 1, wherein

is hydrogen.

34. The compound as claimed in claim 1, wherein

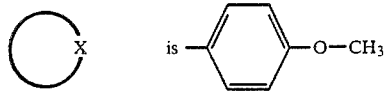

35. The compound as claimed in claim 1, wherein

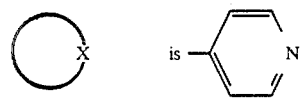

36. The compound as claimed in claim 1, wherein

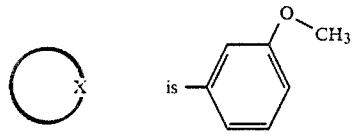

37. The compound as claimed in claim 1, wherein

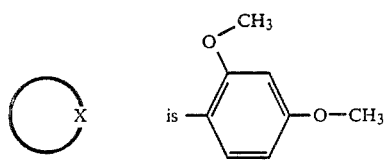

38. The compound as claimed in claim 1, wherein

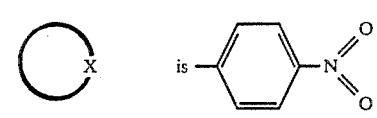

39. The compound as claimed in claim 1, wherein

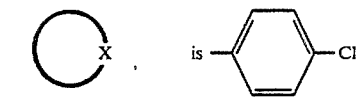

40. The compound as claimed in claim 1, wherein

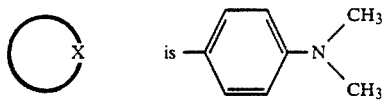

41. The compound as claimed in claim 1, wherein

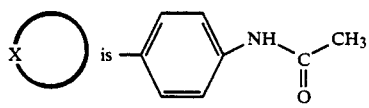 is

42. The compound as claimed in claim 1, wherein

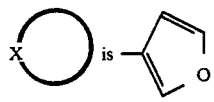

43. The compound as claimed in claim 1, wherein

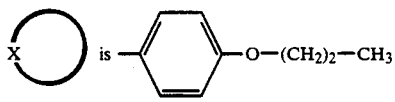

44. The compound as claimed in claim 1, wherein

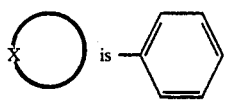

45. The compound as claimed in claim 1, wherein

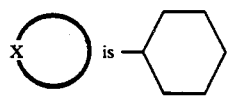

46. The compound as claimed in claim 1, wherein

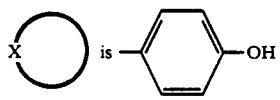

47. The compound as claimed in claim 1, wherein R³ is

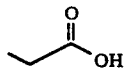

48. The compound as claimed in claim 1, wherein R³ is

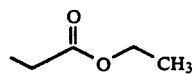

49. A compound as claimed in claim 1, of the formula

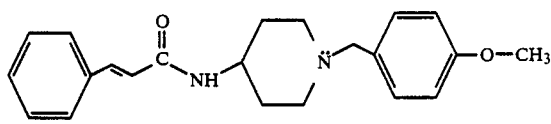

50. A compound as claimed in claim 1, of the formula

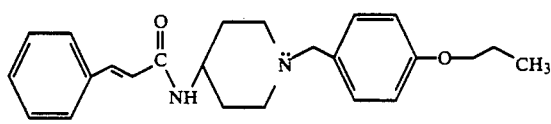

51. A compound as claimed in claim 1, of the formula

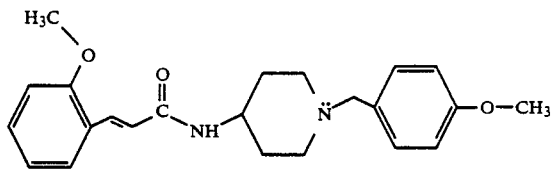

52. A compound as claimed in claim 1, of the formula

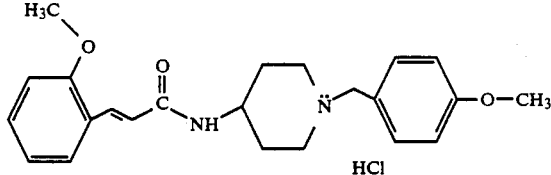

53. A compound as claimed in claim 1, of the formula

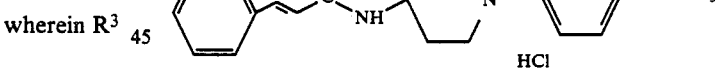

54. A compound as claimed in claim 1, of the formula

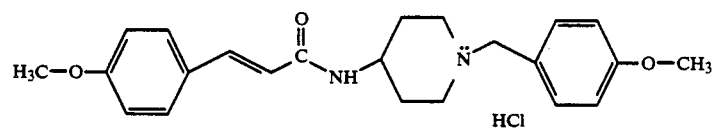

55. A compound as claimed in claim 1, of the formula

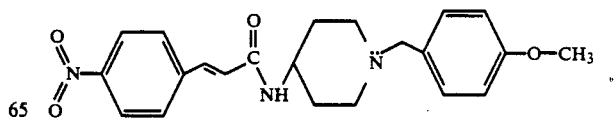

56. A compound as claimed in claim 1, of the formula

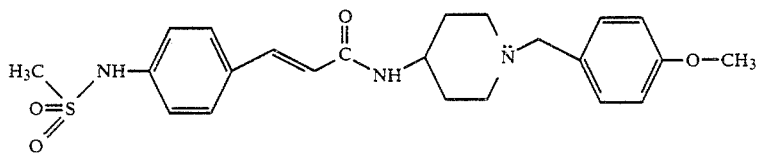

57. A compound as claimed in claim 1, of the formula

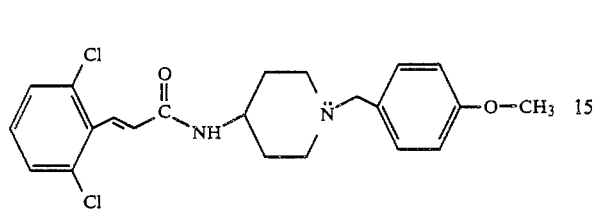

58. A compound as claimed in claim 1, of the formula

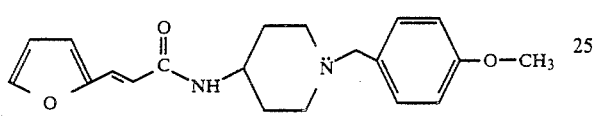

59. A compound as claimed in claim 1, of the formula

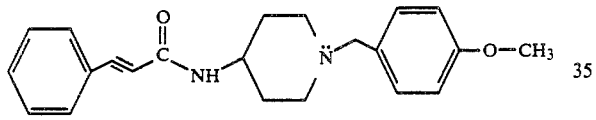

60. A compound as claimed in claim 1, of the formula

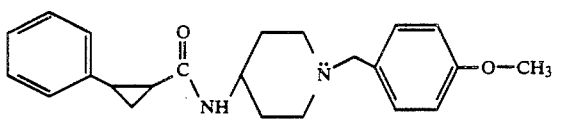

61. A compound as claimed in claim 1, of the formula

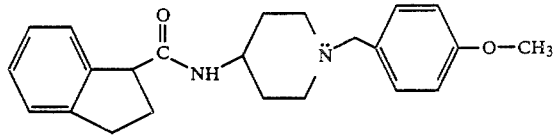

62. A compound as claimed in claim 1, of the formula

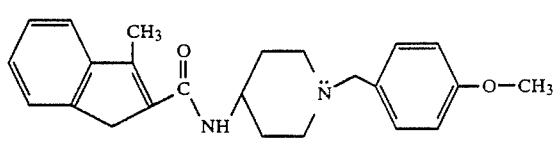

63. A compound as claimed in claim 1, of the formula

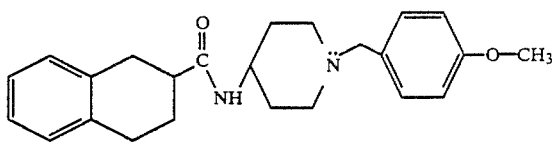

64. A compound as claimed in claim 1, of the formula

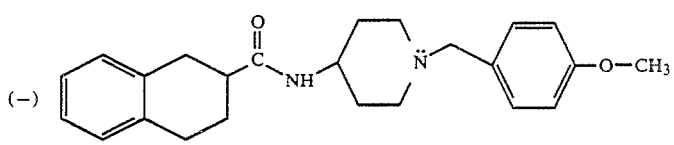

65. A compound as claimed in claim 1, of the formula

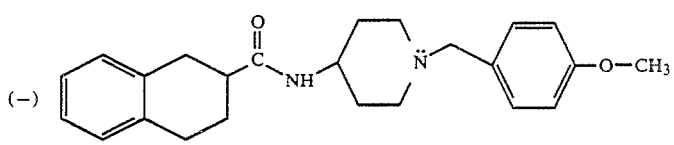

66. A compound as claimed in claim 1, of the formula

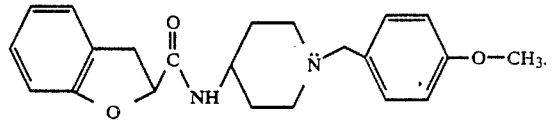

67. A compound as claimed in claim 1, of the formula

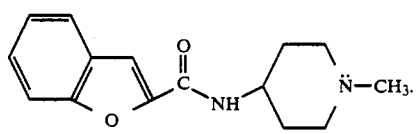

68. A compound as claimed in claim 1, of the formula

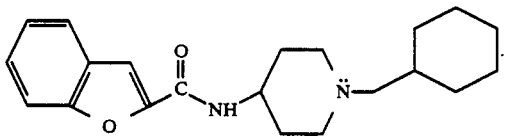

69. A compound as claimed in claim 1, of the formula

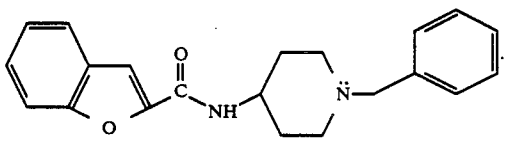

70. A compound as claimed in claim 1, of the formula

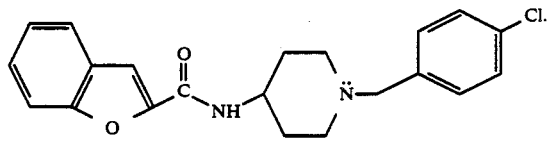

71. A compound as claimed in claim 1, of the formula

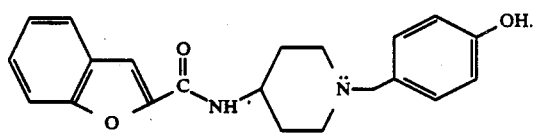

72. A compound as claimed in claim 1, of the formula

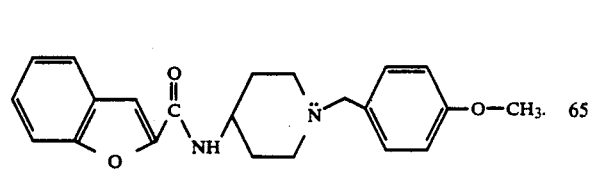

73. A compound as claimed in claim 1, of the formula

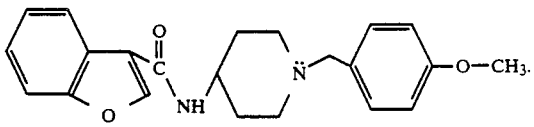

74. A compound as claimed in claim 1, of the formula

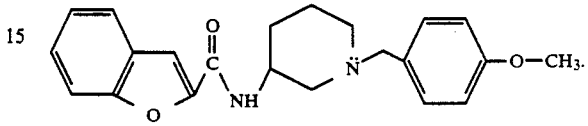

75. A compound as claimed in claim 1, of the formula

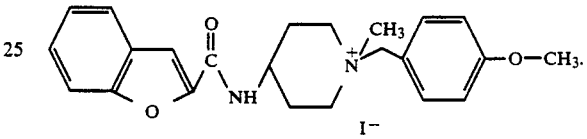

76. A compound as claimed in claim 1, of the formula

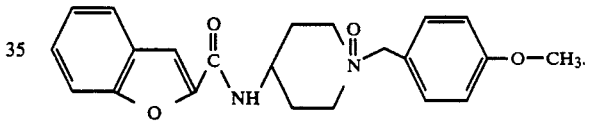

77. A compound as claimed in claim 1, of the formula

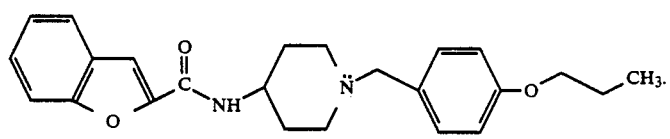

78. A compound as claimed in claim 1, of the formula

79. A compound as claimed in claim 1, of the formula

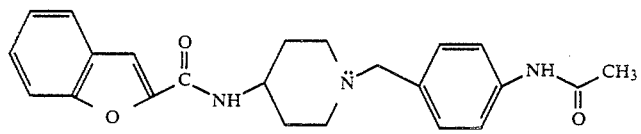

80. A compound as claimed in claim 1, of the formula

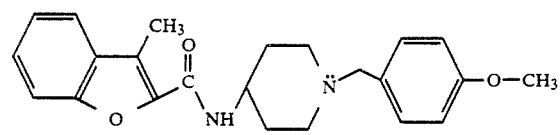

81. A compound as claimed in claim 1, of the formula

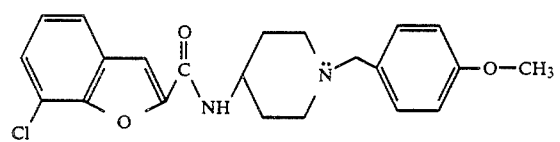

82. A compound as claimed in claim 1, of the formula

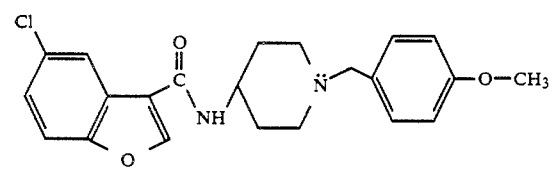

83. A compound as claimed in claim 1, of the formula

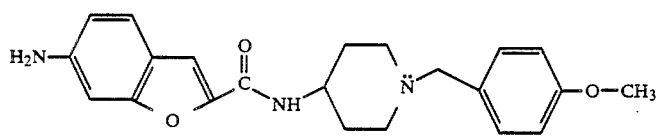

84. A compound as claimed in claim 1, of the formula

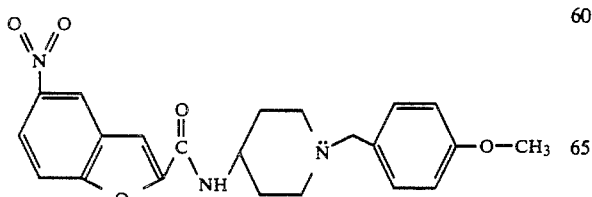

85. A compound as claimed in claim 1, of the formula

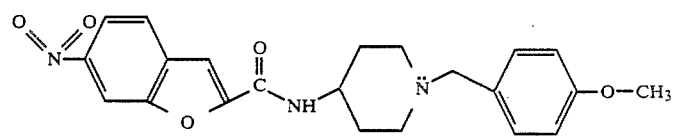

86. A compound as claimed in claim 1, of the formula

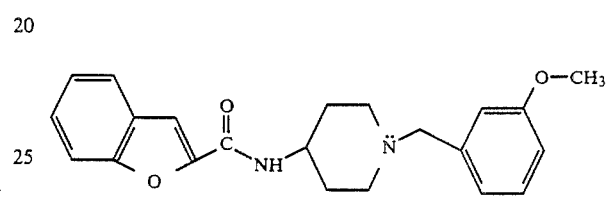

87. A compound as claimed in claim 1, of the formula

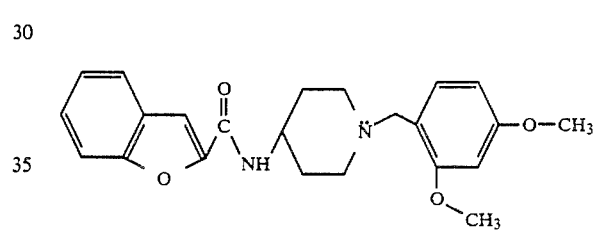

88. A compound as claimed in claim 1, of the formula

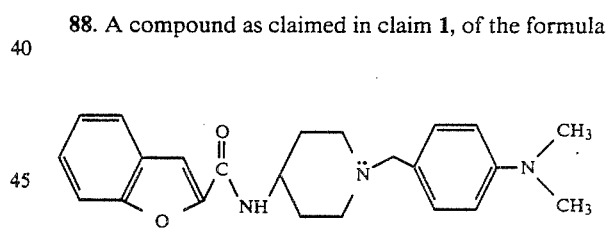

89. A compound as claimed in claim 1, of the formula

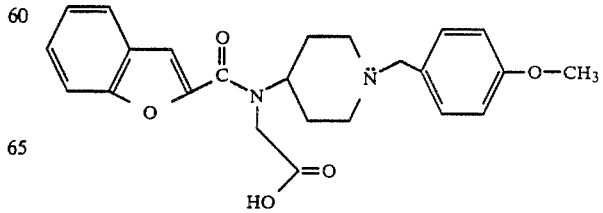

90. A compound as claimed in claim 1, of the formula

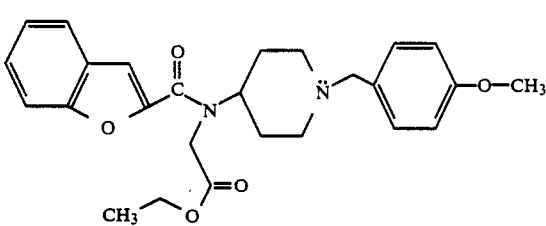

91. A compound as claimed in claim 1, of the formula

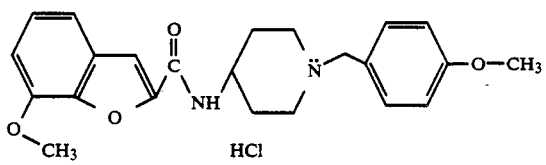

92. A compound as claimed in claim 1, of the formula

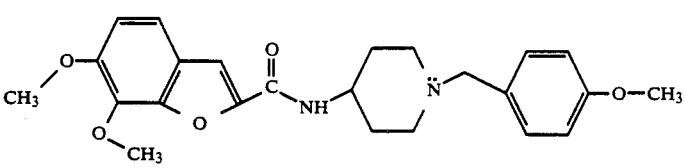

93. A compound as claimed in claim 1, of the formula

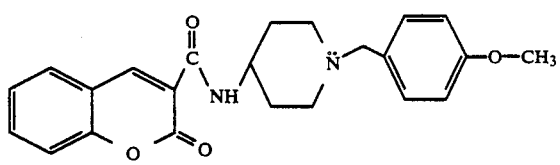

94. A compound as claimed in claim 1, of the formula

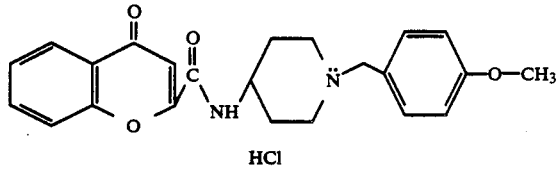

95. A compound as claimed in claim 1, of the formula

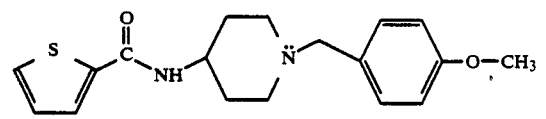

96. A compound as claimed in claim 1, of the formula

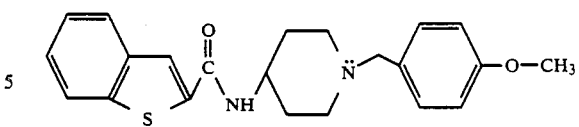

97. A pharmaceutical composition useful for regulating cardiac arrhythmias comprising an effective amount of a compound according to claim 1, together with one or more non-toxic pharmaceutically acceptable carriers.

98. The composition as claimed in claim 97, wherein said compound is N-[1-[(4-methoxyphenyl)methyl]-4-piperidinyl-2E-butenamide.

99. The composition as claimed in claim 97, wherein said compound is N-[1-[(4-methoxyphenyl)methyl]-4-piperidinyl]-3-phenyl-2E-propenamide.

100. The composition as claimed in claim 97, wherein said compound is 3-phenyl-N-[1-[(propoxyphenyl)methyl]-4-piperidinyl]-2E-propenamide.

101. The composition as claimed in claim 97, wherein said compound is 3-(2-methoxyphenyl)-N-[1-[(4-methoxyphenyl)methyl]-4-piperidinyl]-2E-propenamide.

102. The composition as claimed in claim 97, wherein said compound is 3-(2-methoxyphenyl)-N-[1-[(4-methoxyphenyl)methyl]-4-piperidinyl]-2Z-propenamide, monohydrochloride.

103. The composition as claimed in claim 97, wherein said compound is 3-(4-methoxyphenyl)-N-[1-[(4-methoxyphenyl)methyl]-4-piperidinyl]-2E-propenamide.

104. The composition as claimed in claim 97, wherein said compound is N-[1-[(4-methoxyphenyl)methyl]-4-piperidinyl]-3-(4-nitrophenyl)-2E-propenamide.

105. The composition as claimed in claim 97, wherein said compound is N-[1-[(4-methoxyphenyl)methyl]-4-piperidinyl]-3-[4-(methylsulfonyl)amino]phenyl]-2E-propenamide.

106. The composition as claimed in claim 97, wherein said compound is 3-(2,6-dichlorophenyl)-N-[1-[(4-methoxyphenyl)methyl]-4-piperidinyl]-2E-propenamide.

107. The composition as claimed in claim 97, wherein said compound is 3-(2-furanyl)-N-[1-[(4-methoxyphenyl)methyl]-4-piperidinyl]-2E-propenamide.

108. The composition as claimed in claim 97, wherein said compound is N-[1-[(4-methoxyphenyl)methyl]-4-piperidinyl]-3-phenyl-2-propynamide, monohydrochloride.

109. The composition as claimed in claim 97, wherein said compound is. N-[1-[(4-methoxyphenyl)methyl]-4-piperidinyl]-2-phenylcyclopropanecarboxamide.

110. The composition as claimed in claim 97, wherein said compound is 2,3-dihydro-N-[1-[(4-methoxyphenyl)methyl]-4-piperidinyl]-1H-indene-1-carboxamide.

111. The composition as claimed in claim 97, wherein said compound is N-[1-[(4-methoxyphenyl)methyl]-4-piperidinyl]-3-methyl-1H-indene-2-carboxamide.

112. The composition as claimed in claim 97, wherein said compound is (−)1,2,3,4-tetrahydro-N-[1-[(4-methoxyphenyl)methyl]-4-piperidinyl]-2-naphthalenecarboxamide.

113. The composition as claimed in claim 97, wherein said compound is (+)1,2,3,4-tetrahydro-N-[1-[(4-methoxyphenyl)methyl]-4-piperidinyl]-2-naphthalenecarboxamide.

114. The composition as claimed in claim 97, wherein said compound is 2,3-dihydro-N-[1-[(4-methoxyphenyl)methyl]-4-piperidinyl]-2-benzofurancarboxamide.

115. The composition as claimed in claim 97, wherein said compound is N-(1-methyl-4-piperidinyl)-2-benzofurancarboxamide.

116. The composition as claimed in claim 97, wherein said compound is N-[1-(cyclohexylmethyl)-4-piperidinyl]-2-benzofuracarboxamide.

117. The composition as claimed in claim 97, wherein said compound is N-[1-(phenylmethyl)-4-piperidinyl]-2-benzofurancarboxamide.

118. The composition as claimed in claim 97, wherein said compound is N-[1-[(4-chlorophenyl)methyl]-4-piperidinyl]-2-benzofurancarboxamide.

119. The composition as claimed in claim 97, wherein said compound is N-[1-[(4-hydroxyphenyl)methyl]-4-piperidinyl]-2-benzofurancarboxamide.

120. The composition as claimed in claim 97, wherein said compound is N-[1-[(4-methoxyphenyl)methyl]-4-piperidinyl]-2-benzofurancarboxamide.

121. The composition as claimed in claim 97, wherein said compound is N-[1-[(4-methoxyphenyl)methyl]-4-piperidinyl]-3-benzofurancarboxamide.

122. The composition as claimed in claim 97, wherein said compound is N-[1-[(4-methoxyphenyl)methyl]-3-piperidinyl]-2-benzofurancarboxamide.

123. The composition as claimed in claim 97, wherein said compound is 4-[(2-benzofuranylcarbonyl)amino]-1-[(4-methoxyphenyl)methyl]-1-methylpiperidinium iodide.

124. The composition as claimed in claim 97, wherein said compound is N-[1-[(4-methoxyphenyl)methyl]-4-piperidinyl]-2-benzofurancarboxamide, N-oxide.

125. The composition as claimed in claim 97, wherein said compound is N-[1-[(4-propoxyphenyl)methyl]-4-piperidinyl]-2-benzofurancarboxamide.

126. The composition as claimed in claim 97, wherein said compound is N-[1-[(4-nitrophenyl)methyl]-4-piperidinyl]-2-benzofurancarboxamide.

127. The composition as claimed in claim 97, wherein said compound is N-[1-[(4-(acetylamino)phenylmethyl]-4-piperidinyl]-2-benzofurancarboxamide.

128. The composition as claimed in claim 97, wherein said compound is N-[1-[(4-methoxyphenyl)methyl]-4-piperidinyl]-3-methyl-2-benzofurancarboxamide.

129. The composition as claimed in claim 97, wherein said compound is 7-chloro-N-[1-[(4-methoxyphenyl)methyl]-4-piperidinyl]-2-benzofurancarboxamide.

130. The composition as claimed in claim 97, wherein said compound is 5-chloro-N-[1-[(4-methoxyphenyl)methyl]-4-piperidinyl]-2-benzofurancarboxamide.

131. The composition as claimed in claim 97, wherein said compound is N-[1-[(4-methoxyphenyl)methyl]-4-piperidinyl]-5-nitro-2-benzofurancarboxamide.

132. The composition as claimed in claim 97, wherein said compound is 7-methoxy-N-[1-[(4-methoxyphenyl)methyl]-4-piperidinyl]-2-benzofurancarboxamide, monohydrochloride.

133. The composition as claimed in claim 97, wherein said compound is 6,7-dimethoxy-N-[1-[(4-methoxyphenyl)methyl]-4-piperidinyl]-2-benzofurancarboxamide.

134. The composition as claimed in claim 97, wherein said compound is N-[1-[(4-methoxyphenyl)methyl]-4-piperidinyl]-2-oxo-2H-1-benzopyran-3-carboxamide.

135. The composition as claimed in claim 97, wherein said compound is N-[1-[(4-methoxyphenyl)methyl]-4-piperidinyl]-4-oxo-4H-1-benzopyran-3-carboxamide, monohydrochloride.

136. The composition as claimed in claim 97, wherein said compound is N-[1-[(4-methoxyphenyl)methyl]-4-piperidinyl]-2-thiophenecarboxamide.

137. The composition as claimed in claim 97, wherein said compound is N-[1-[(4-methoxyphenyl)methyl]-4-piperidinyl]-2-benzo[b]thiophenecarboxamide.

138. A method of regulating cardiac arrhythmias in a mammal, comprising administering to said mammal a pharmacologically effective amount of a compound as claimed in claim 1.

139. A method of prolonging repolarization of cardiac cells during a cardiac action potential, comprising administering to said mammal a pharmacologically effective amount of a compound as claimed in claim 1.

* * * * *

UNITED STATES PATENT AND TRADEMARK OFFICE
CERTIFICATE OF CORRECTION

PATENT NO. : 5,098,915
DATED : March 24, 1992
INVENTOR(S) : Desai, et al.

It is certified that error appears in the above-identified patent and that said Letters Patent is hereby corrected as shown below:

Column 1, line 63, reading "arylcyloalkyl" should read -- arylcycloalkyl --.

Column 9, last structure, reading

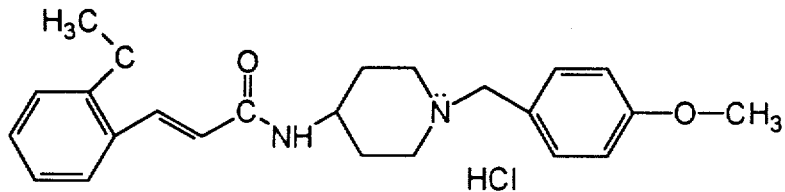

should read

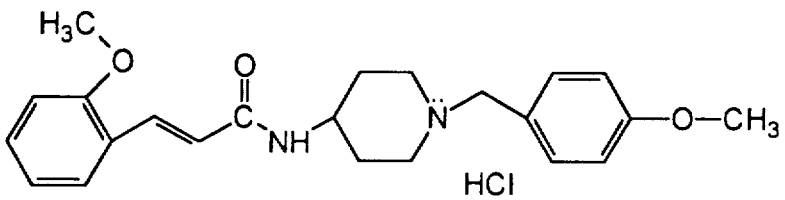

Column 13, last structure, reading

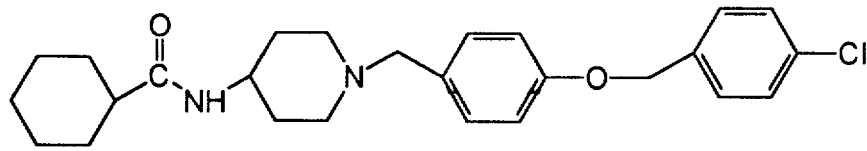

UNITED STATES PATENT AND TRADEMARK OFFICE
CERTIFICATE OF CORRECTION

PATENT NO. : 5,098,915
DATED : March 24, 1992
INVENTOR(S) : Desai, et al.

It is certified that error appears in the above-identified patent and that said Letters Patent is hereby corrected as shown below:

should read

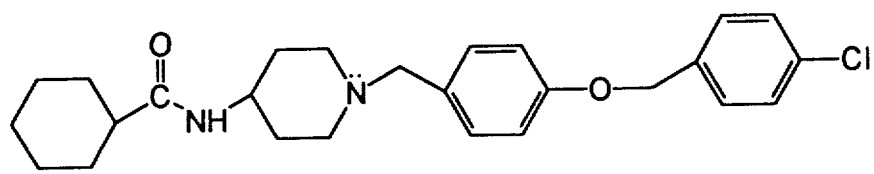

Signed and Sealed this

Seventeenth Day of May, 1994

Attest:

BRUCE LEHMAN

Attesting Officer           Commissioner of Patents and Trademarks